US012205698B2

(12) United States Patent
Booth et al.

(10) Patent No.: US 12,205,698 B2
(45) Date of Patent: *Jan. 21, 2025

(54) ADVISING DIABETES MEDICATIONS

(71) Applicant: Aseko, Inc., Greenville, SC (US)

(72) Inventors: Robert C. Booth, Greer, SC (US);
Andrew Rhinehart, Greenville, SC (US); Harry Hebblewhite, Atlanta, GA (US)

(73) Assignee: Aseko, Inc., Greenville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/426,250

(22) Filed: Jan. 29, 2024

(65) Prior Publication Data

US 2024/0170123 A1 May 23, 2024

Related U.S. Application Data

(63) Continuation of application No. 18/352,046, filed on Jul. 13, 2023, now Pat. No. 11,908,561, which is a continuation of application No. 18/089,380, filed on Dec. 27, 2022, now Pat. No. 11,728,022, which is a
(Continued)

(51) Int. Cl.
| | |
|---|---|
| *G16H 20/13* | (2018.01) |
| *G16H 10/60* | (2018.01) |
| *G16H 20/17* | (2018.01) |
| *G16H 40/63* | (2018.01) |
| *G16H 50/20* | (2018.01) |
| *G16H 50/30* | (2018.01) |

(52) U.S. Cl.
CPC ............ *G16H 20/13* (2018.01); *G16H 10/60* (2018.01); *G16H 20/17* (2018.01); *G16H 40/63* (2018.01); *G16H 50/20* (2018.01); *G16H 50/30* (2018.01)

(58) Field of Classification Search
None
See application file for complete search history.

(56) References Cited

U.S. PATENT DOCUMENTS

2007/0179434 A1 8/2007 Weinert et al.
2008/0306353 A1* 12/2008 Douglas ................ G16H 40/63
600/301
2009/0171697 A1 7/2009 Glauser et al.
(Continued)

OTHER PUBLICATIONS

International Search Report and Written Opinion for the related application No. PCT/US2018/066025 dated Apr. 18, 2019.

*Primary Examiner* — Robert W Morgan
*Assistant Examiner* — Edward B Winston, III
(74) *Attorney, Agent, or Firm* — Honigman LLP; Brett A. Krueger; Grant Griffith

(57) ABSTRACT

A method includes obtaining prescribing drug information and published guidelines for each of a plurality of ADMs available for managing glucose levels, and receiving patient information associated with a patient. The method also includes ordering total demerit values from lowest to highest, selecting a predetermined number of recommended ADMs associated with the lowest total demerit values, and determining a recommended dosage for each recommended ADM. The method also includes transmitting a therapy regimen to a patient device associated with the patient. The therapy regimen includes the recommended ADMs and the recommended dosage for each recommended ADM.

20 Claims, 19 Drawing Sheets

Related U.S. Application Data continuation of application No. 16/222,415, filed on Dec. 17, 2018, now Pat. No. 11,568,974.

(60) Provisional application No. 62/609,326, filed on Dec. 21, 2017.

(56) References Cited

U.S. PATENT DOCUMENTS

| | | | | |
|---|---|---|---|---|
| 2010/0138453 | A1* | 6/2010 | Alferness | G16H 50/50 |
| | | | | 707/803 |
| 2010/0198020 | A1* | 8/2010 | Alferness | G16H 20/60 |
| | | | | 600/300 |
| 2010/0292634 | A1* | 11/2010 | Kircher, Jr. | G16H 20/13 |
| | | | | 604/66 |
| 2012/0286953 | A1* | 11/2012 | Bousamra | G16H 50/70 |
| | | | | 702/19 |
| 2013/0317316 | A1* | 11/2013 | Kandeel | G16H 50/50 |
| | | | | 600/300 |
| 2014/0032196 | A1* | 1/2014 | Albisser | G16H 15/00 |
| | | | | 703/11 |
| 2014/0181128 | A1* | 6/2014 | Riskin | G06F 16/3344 |
| | | | | 707/756 |
| 2016/0324481 | A1 | 11/2016 | Christensen et al. | |
| 2017/0053101 | A1 | 2/2017 | Booth et al. | |
| 2017/0232204 | A1* | 8/2017 | Knapp | A61J 7/0436 |
| | | | | 604/66 |
| 2017/0242962 | A1 | 8/2017 | Lenchitsky | |
| 2017/0286638 | A1* | 10/2017 | Searle | G16H 40/63 |
| 2018/0353698 | A1* | 12/2018 | Saint | A61M 5/31546 |

* cited by examiner

Patients

| Patient ID No. | Last Name | First Name | Date of Birth | DM Type | Gender | Date Dx DM |
|---|---|---|---|---|---|---|
| 1 | Doe | John | 3/4/1952 | 2 | M | 5/1/2006 |
| 2 | Typical | Tilly | 6/21/1975 | 1 | F | 3/12/1978 |
| 3 | Mann | Super | 5/28/1936 | 2 | M | 4/21/1985 |

FIG. 3A

Permanent Conditions

| Patient ID No. | Condition | Condition Index |
|---|---|---|
| 2 | Hyopthyroid | 7 |
| 2 | Amputation - Rt. Leg | 16 |
| 2 | Maculer Degeneration | 7 |

FIG. 3B

Patient Preferences (410)

| Update_Date-Time | HCP | BG_Target | A1c_Target | ADM_$_perMo_Low | ADM_$_perMo_Hi | Cost_Importance | Weight_Importance | Complexity_Importance | Efficacy_Importance | Mealtime_Coverage_Importance | Hypoglycemia_Importance |
|---|---|---|---|---|---|---|---|---|---|---|---|
| 6/3/2016 | Seus | 100 | 6.5 | $50 | $180 | 0 | 0 | 1 | 1 | 1 | 1 |
| 6/17/2016 | Pepper | 100 | 6.5 | $50 | $180 | 1 | 0 | 1 | 1 | 1 | 1 |
| 6/28/2016 | Livingston | 100 | 6.5 | $50 | $180 | 1 | 1 | 1 | 1 | 1 | 1 |

Allergies and Exclusions (420)

| Update_dateTime-Linked | ADM_Index | Drug_Name | Allergic_or_Exclude |
|---|---|---|---|
| (linked) | 8 | Sulfonlylurea | Allergic |
| (linked) | 21 | Plioglitazone | Exclude |

FIG. 4B

Current Medications (430)

| Update_dateTime-Linked | ADM_Index | Current_Drugs | Current_Dose_ea | Dose_units | Current_Doses/Day | Rx_Compliance |
|---|---|---|---|---|---|---|
| (linked) | 5 | Metformin | 500 | mg | 1 | 0.90 |
| (linked) | non-ADM | Solumedrol | 21 | μg | 1 | 0.64 |
| (linked) | non-ADM | Synthroid | 80 | μg | 2 | 0.90 |

| Patient Device Calibration | | | | | | | | | |
|---|---|---|---|---|---|---|---|---|---|
| Device | Date_of_Calibration | Calories-per-mile-by-run-steps | Run-steps-per-mile | Calories-per-mile-by-Walk-steps | Walk-steps-per-mile | Calories-per_Mile-by-GPS | Calories-per-stairstep | Calories-per-rep_elliptical | Calories-per-rep-per-Lb_WeightMachine_A |
| Fitness Tracker 110c | 6/20/2017 | 40.0 | 1760.0 | -35 | 2300 | -41 | -0.04 | -0.03 | -0.04 |
| Phone 110b | 6/20/2017 | 41.0 | 1654.0 | -37 | 2500 | -42 | -0.04 | -0.03 | -0.04 |
| BG Monitor 124 | 6/20/2017 | | | | | | | | |
| Bottle 123c | 6/20/2017 | | | | | | | | |
| Scale | 6/20/2017 | | | | | | | | |

| Patient Device Data | | | | | | | | | | | | | | | |
|---|---|---|---|---|---|---|---|---|---|---|---|---|---|---|---|
| Device | Date-of-Update | Miles-by-Run-step_wk | Run-steps_wk | Calories-by_Run-steps_wk | Miles-by-GPS_wk | Calories-by_GPS_wk | Elliptical-reps_wk | Calories-by_Elliptical_wk | WeightMachine_A-reps_wk | WeightMachine_A-WgtLoad | Calories-by_WeightMachine_A_wk | Calories_Eaten_wk | Carbs_Eaten_wk | Bottle-Openings_wk | eWeight_kg |
| Fitness Tracker 110c | 6/20/2017 | 4.0 | 7040 | 160 | | | 7 | | 200 | 100 | | | | | |
| Phone 110b | 6/20/2017 | 5.0 | 8270 | 205 | | 16 | | | 200 | 100 | | 3360 | 1680 | | |
| BG Moinitor 124 | 6/20/2017 | | | | | | | | | | | 3200 | 1600 | | |
| Bottle 123c | 6/20/2017 | | | | | | | | | | | | | 14 | |
| Scale 125 | 6/20/2017 | | | | | | | | | | | | | | 90 |

FIG. 4E

| Current Conditions | | | | | | | |
|---|---|---|---|---|---|---|---|
| 460 ⤴ Lab Test: ▼ | | Low Limit | High Limit | Result | Date | Associated Condition | HCP Assessment Positive? |
| Glucose | (mg/dL) | 70 | 180 | 176 | 5/6/2017 * | Hyperglycemia | (•) ⤴ 462 |
| Potassium | (units) | xx | xx | | | | ( ) |
| A1c | (%) | none | 7 | 8 | 4/15/2017 | Hyperglycemia | (•) ⤴ 462 |
| Fructosamine | (units) | xx | xx | | | | ( ) |
| Anion Gap | (units) | xx | xx | | | | ( ) |
| Beta-hydroxybutyrate | (units) | xx | xx | | | | ( ) |
| eGFR | (%) | 30% | none | 55 | 6/28/2016 | Contra | ( ) |
| C-peptide | (units) | xx | xx | 0.45 | 3/7/2015 | Type 2 | ( ) |
| Islet Cell Antibodies (ICA) | (units) | xx | xx | | | | ( ) |
| B-type natriuretic peptide | (units) | xx | xx | | | | ( ) |
| G6PD deficienc | (units) | xx | xx | | | | ( ) |
| GAD | (units) | xx | xx | 54 | 5/6/2017 * | | ( ) |
| Liver profile (AST,ALT, Bilirubin) (units) | | xx | xx | | | | ( ) |
| Amylase | (units) | xx | xx | | | | ( ) |
| Lipase | (units) | xx | xx | | | | ( ) |
| Triglycerides | (units) | xx | xx | | | | ( ) |
| >> (add a Lab result) | | | | | | | ( ) |

Note: * Date shown is auto-filled date of entry.

FIG. 4F

| Current Labs | | | |
|---|---|---|---|
| Update_dateTime (from link) | Lab_index | Lab_Name | Lab_Value |
| 6/28/2016 | 5 | TSH | 23 |
| 6/28/2016 | 1 | A1c | 8 |
| 6/28/2016 | 6 | GFR | 55 |
| 6/28/2016 | 2 | Weight | 95 |
| 6/28/2016 | 3 | Height | 170 |

FIG. 4G

| ADM_index | FDA-NDC | ADM_Class | ADM_Name-Generic | Delivery_Method | Start_Dose | Max_Dose | Units_of_measure | Scaled_EFFICACY | Scaled_HYPO-Risk | Scaled_WEIGHT_Effect | Scaled_COST | Scaled_COMPLEXITY | Scaled_Mealtime_Coverage |
|---|---|---|---|---|---|---|---|---|---|---|---|---|---|
| 1 | | | | No Change | | | | | | | | | |
| 5 | 5215-456 | Biguanides | Metformin | pill | 1000 | 2000 | mg/day | 0.5 | 0.0 | 0.5 | 0.1 | 0.1 | 0.1 |
| 6 | 3461-234 | GLP-1 recep ag | Exenatide | SubQ | | | | 0.5 | 0.0 | 0.1 | 0.9 | 0.6 | 0.1 |
| 7 | 5125-961 | Sulfonylurea | Glipizide | pill | | | | 0.9 | 0.9 | 0.9 | 0.1 | 0.1 | 0.1 |

Anti-Diabetes Medications 510

FIG. 5A

Drug Interactions

| ADM_Index | Drug-IntrX-index | Class | Generic | Interaction(0,1) |
|---|---|---|---|---|
| 5 | (null) | (null) | (null) | (null) |
| 5 | (null) | (null) | (null) | (null) |
| 5 | (null) | (null) | (null) | (null) |

FIG. 5B

Available Dosages

| ADM_Index | Class | Generic | Dose_ea | units_measure |
|---|---|---|---|---|
| 5 | (null) | (null) | 500 | mg |
| 5 | (null) | (null) | 850 | mg |
| 5 | (null) | (null) | 100 | mg |

FIG. 5C

Contraindications

| ADM_Index (link) | Medical_Condition_Index | Medical_Condition_name | Lab_Index | Lab_Name | Lab_Lo_Limit | Lab_Hi_Limit | Conditional_Start_Daily_Dose | Condition_Type | Side_Effects |
|---|---|---|---|---|---|---|---|---|---|
| 5 | 4 | eGFR_45to60 | 6 | GFR | 45% | 60% | 1000 | Contra | |
| 5 | 5 | eGFR_30to45 | 6 | GFR | 30% | 45% | 0 | Contra | |
| 5 | 6 | eGFR_LT30 | 6 | GFR | 0 | 30% | 0 | Contra | |
| 8 | 10 | Hypo Risk | | | | | | Side_Effect | Risk of Hypoglycmia |
| 9 | 12 | Nausea Risk | | | | | | Side_Effect | May cause Nausea |

| Guideline Refreshment Conversion Process ||||
| Guideline Parameter | Source: ADA Guidelines (verbal) Guideline | Output Scaled Guideline | Name |
| --- | --- | --- | --- |
| Efficacy | Intermediate | 0 | Scaled_Efficacy |
| Efficacy | High | 0.5 | |
| Efficacy | Highest | 1 | |
| Hypo Risk | Low | 0 | Scaled_Hypo_Risk |
| Hypo Risk | Moderate | 0.5 | |
| Hypo Risk | High | 1 | |
| Weight_Effect | Loss | 0 | Scaled Weight_Effect |
| Weight_Effect | Neutral | 0.5 | |
| Weight_Effect | Gain | 1 | |
| Cost | Low | 0 | Scaled_Cost |
| Cost | Variable | 0.5 | |
| Cost | High | 1 | |
| Complexity | oral 1/day | 0 | Scaled_Complexity |
| Complexity | oral 2/day | 0.2 | |
| Complexity | oral 3/day | 0.4 | |
| Complexity | Injection 1/day | 0.6 | |
| Complexity | Injection 2/day | 0.8 | |
| Complexity | Injection 3/day | 1 | |
| Meal_Coverage | coverage | 1 | Scaled_Meal_Coverage |
| Meal_Coverage | no coverage | 0 | |

FIG. 5F

| Configurable Constants ||
| Constant | Assigned Value |
| --- | --- |
| Adverse Demerit | 60 |
| Instruction Demerit | 30 |
| Guideline Demerit | 10 |
| N_Finalists | 3 |
| Calories_Per_Carb | 4 |

FIG. 5G

Allergies and Conditions Screen 620

| Is patient allergic or intolerant to these ADM's? ▶ | | | | | (Blanks are OK. They are addressed by the program.) | | |
|---|---|---|---|---|---|---|---|
| Insulin Only ( ) | | Show ( ) | | | | Lab & Current Conditions | HCP's Final Exclude |
| Sort (•) | Sort ( ) | Sort ( ) | Alergic | Avoid Side-Effects | Sort ( ) | | |
| Class | Generic | Brand | | | Listed Side-effects | | |
| Biguanides | Metformin | | (•) | (•) | Gas | (Y) | (•) |
| Bile acid sequestrants | Colesevelam | | ( ) | | | (n) | ( ) |
| Dopamine-2 agonists | Bromocriptine (quick release) | | ( ) | | | (n) | ( ) |
| DPP-4 inhibitors | Alogliptin | | ( ) | | | (n) | ( ) |
| GLP-1 receptor agonists | Albiglutide | | ( ) | | | (n) | ( ) |
| GLP-1 receptor agonists | Exenatide | | ( ) | (•) | Nausea | (n) | (•) |
| Meglitinides (glinides) | Nateglinide | | ( ) | | | (n) | ( ) |
| SGLT2 inhibitors | Canagliflozin | | ( ) | (•) | Genital Mycotic infection | (n) | (•) |
| Sulfonylureas | Gliclazide | | (•) | ( ) | Hypoglycemia | (n) | (•) |
| Sulfonylureas | Glimepiride | | (•) | ( ) | Hypoglycemia | (n) | (•) |
| Sulfonylureas | Glipizide | | ( ) | ( ) | Hypoglycemia | (n) | ( ) |
| Sulfonylureas | Glyburide/Glibenclamide | | ( ) | ( ) | Hypoglycemia | (n) | ( ) |
| TZDs | Pioglitazone | | ( ) | ( ) | Congestive Heart Failure, CHF | (n) | ( ) |
| Insulin, Rapid-Acting | (keyed to Brand) | | ( ) | ( ) | Hypoglycemia | (n) | ( ) |
| Insulin, Regular | (keyed to Brand) | | ( ) | ( ) | Hypoglycemia | (n) | ( ) |
| Insulin, Long-Acting | (keyed to Brand) | | ( ) | ( ) | Hypoglycemia | (n) | ( ) |
| Insulin, Inhaled | (keyed to Brand) | | ( ) | ( ) | Hypoglycemia | (n) | ( ) |
| Insulin, Inhaled | (keyed to Brand) | | ( ) | ( ) | Chronic Lung Disease | (n) | ( ) |

FIG. 6B

Energy Based Dosage Screen 630

Energy-based Dose Adjustment:

411b — A1c Target: [ % ]
632 — Current A1c: [ % ]

634 — A1c shows: Patient's Surplus (calories/wk): [ 2500 ]

Changes to Energy-Budget:

| | Load or NA | Current Average | Change | Calorie Change /wk |
|---|---|---|---|---|
| Fitbit Miles (run-step per wk) ▼ | NA | 10 | + 4 | - 500 |
| Carbs per meal (gm/day) ▼ | NA | 300 | -20 | - 1680 |
| Weight Machine A (reps/wk) ▼ | 100 | 200 | +50 | - 50 |

635

⋮

| Energy-Change Method (units) ▼ | eg. Lbs | XXX | +-Y | +- ZZ |

636 — Remaining Enargy Surplus (calories/wk): [ +270 ]

611 — Energy-Adjusted A1c: [ % ]

FIG. 6C

ADM Selection Screen 640

Energy-Based Treatment Information 642

- Increase Run to 9 miles/week
- Decrease Meals to 80 grams of carbohydrates

Recommended ADM Listing 644     646     648

- SGLT-2 Inhibitors 810, 810a → Jardiance (empagliflozon)   27mg    95% match Reduce A1c by 0.7-1.3%

644 → Notes:
Weight Loss          Raises LOL-C          Lower Blood
Little/No Nausea     Raises creatinine     pressure 810, 810b → Invokana (canegliflozin)   50mg    90% match Reduce A1c by 0.7-1.3%

Notes:
Weight Loss          Lower Blood
Little/No Nausea     pressure

- Basal Insulins 810, 810c → Lantus (glargine U-100)   50mg    95% match

Limitless A1c reduction

Notes:
Weight Loss          Little/No Nausea ( Open Table )  649

FIG. 6D

ADM Selection Table 800

| | | | Adverse Demerits | Instruction Demerits | Guide Demerits | Modified Demerits | Total Demerits | Dose Note 1 | Dose Note 2 |
|---|---|---|---|---|---|---|---|---|---|
| Insulin Only ( ) | | | 812a | 812b | 812c | 812d | 812e | 814a | 814b |
| Sort (●) | Sort ( ) | | | | | | | | |
| Class | Generic | | | | | | | | |
| Biguanides | Metformin | | 0 | 0 | 0 | -200 | 0 | | |
| Bile acid sequestrants | Colesevelam | | 0 | 0 | 0 | 0 | 0 | | |
| Dopamine-2 agonists | Bromocriptine (quick release) | | 0 | 0 | 0 | 0 | 0 | | |
| DPP-4 inhibitors | Alogliptin | | 0 | 0 | 0 | 0 | 0 | | |
| GLP-1 receptor agonists | Exenatide | | 0 | 0 | 0 | 0 | 0 | | |
| Meglitinides (glinides) | Nateglinide | | 0 | 0 | 0 | 0 | 0 | | |
| SGLT2 inhibitors | Canagliflozin | | 0 | 0 | 0 | 0 | 0 | | |
| Sulfonylureas | Gliclazide | | 60 | 0 | 0 | 0 | 0 | | |
| TZDs | Pioglitazone | | 60 | 0 | 0 | 0 | 0 | | |

# ADVISING DIABETES MEDICATIONS

CROSS REFERENCE TO RELATED APPLICATIONS

This U.S. patent application is a continuation of, and claims priority under 35 U.S.C. § 120 from, U.S. patent application Ser. No. 18/352,046, filed on Jul. 13, 2023, which is a continuation of U.S. patent application Ser. No. 18/089,380, filed on Dec. 27, 2022, which is a continuation of U.S. patent application Ser. No. 16/222,415, filed on Dec. 17, 2018, which claims priority under 35 U.S.C. § 119(e) to U.S. Provisional Application 62/609,326, filed on Dec. 21, 2017. The disclosures of these prior applications are considered part of the disclosure of this application and are hereby incorporated by reference in their entirety.

TECHNICAL FIELD

This disclosure relates to managing anti-diabetes medications (ADMs).

BACKGROUND

Diabetes is among the most prevalent and expensive medical conditions that requires prescription therapy. Managing diabetes requires maintaining glucose levels within a prescribed goal range. For patients with type 1 diabetes, where the production of insulin is impaired, the affected individual must regularly inject insulin into the body to maintain control glucose levels. In contrast to type 1 diabetes, individuals having type 2 diabetes may produce insulin; however, the pancreas may not secrete enough insulin and/or the cells of the body may be insulin resistant. Accordingly, type 2 diabetes may be treated with one or more of: insulin injections; lifestyle changes, such as exercise and diet; and anti-diabetes medications (ADMs).

Anti-diabetes medications may include agents configured to increase the amount of insulin secreted by the pancreas, lower resistance of the target organs to insulin, and/or lower a rate at which glucose is absorbed from the gastrointestinal tract. Selection of anti-diabetes medications generally includes consideration of a variety of factors, including cost, efficacy, effectiveness, complexity of administration, patient lifestyle, interactions of the medication with other medications, and potential side effects, for example. Accordingly, selection and management of ADMs in combination with other treatment options can be complex.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's glucose level is below a preferred target. Appropriate management of glucose levels for critically ill patients reduces co-morbidities and is associated with a decrease in infection rates, length of hospital stay, and death. The treatment of hypoglycemia may differ depending on whether or not a patient has been diagnosed with Type 1 diabetes mellitus, Type 2 diabetes mellitus, gestational diabetes mellitus, or non-diabetic stress hypoglycemia. The glucose target range $BG_{TR}$ is defined by a lower limit, i.e., a low target $BG_{TRL}$, and an upper limit, i.e., a high target $BG_{TRH}$.

SUMMARY

One aspect of the disclosure provides a method for determining a therapy regimen. The method includes obtaining, by data processing hardware, prescribing drug information and published guidelines for each of a plurality of Anti-Diabetes Medications (ADMs) available for managing glucose levels and receiving, at the data processing hardware, patient information associated with a patient seeking selection and dosing of one or more of the available ADMs. For each of the available ADMs, the method further includes: determining, by the data processing hardware, an adverse demerit value, a guideline demerit value, and an instruction demerit value based on the patient information, the prescribing drug information, and the published guidelines for the corresponding available ADM; and determining, by the data processing hardware, a total demerit value by summing the adverse demerit value, the guideline demerit value, and the instruction demerit value. The method also includes ordering, by the data processing hardware, the total demerit values for the available ADMs from lowest to highest; selecting, by the data processing hardware, a predetermined number of recommended ADMs associated with the lowest total demerit values from the plurality of available ADMs; determining, by the data processing hardware, a recommended dosage for each recommended ADM based on the patient information, the prescribing drug information, and the published guidelines; and transmitting the therapy regimen from the data processing hardware to a patient device associated with the patient. The therapy regimen includes the recommended ADMs and the recommended dosage for each recommended ADM.

Implementations of the disclosure may include one or more of the following optional features. In some implementations, the patient information includes at least one of treatment preference information, treatment guideline ratings, a current medications list, current medical conditions associated with the patient, permanent medical conditions associated with the patient, one or more glucose values for the patient, or an A1c value for the patient. The treatment preference information includes at least one of a target glucose range for the patient, a target A1c value for the patient, a preferred minimum monthly treatment cost, or a preferred maximum monthly treatment cost. The treatment guideline ratings are each assigned by the patient and measure a subjective level of importance to the patient for a corresponding treatment guideline. The treatment guideline ratings include at least one of a cost rating, a body weight rating, a treatment regimen complexity rating, a treatment efficacy rating, a mealtime coverage needs rating, or a hypoglycemia rating. The current medications list includes a list of medications and corresponding dosages the patient is currently prescribed. The one or more glucose values for the patient are measured by a glucometer or a continuous glucose monitor in communication with the data processing hardware.

The method may include receiving, at the data processing hardware, exercise data and adjusting, by the data processing hardware, the recommended dosage for at least one of the recommended ADMs based on the received exercise data. The exercise data may be received from a fitness tracker associated with the patient. In some implementations, determining the adverse demerit value includes obtaining one or more contraindicating conditions associated with the corresponding available ADM based on the prescribing drug information and the published guidelines, obtaining a list of medications that interact with the corresponding available ADM based on the prescribing drug information, determining whether the patient currently has any of the contraindicating conditions associated with the corresponding available ADM based on the patient information that includes lab results associated with the patient, determining whether the patient is currently taking at least one of the medications that interact with the corresponding available ADM based on the patient information that include a list of medications the patient is currently taking, assigning an adverse demerit increment value when the patient currently has any of the contraindicating conditions associated with the corresponding available ADM, assigning the adverse demerit increment value when the patient is currently taking at least one of the medications that interact with the corresponding available ADM, and determining the adverse demerit value for the corresponding available ADM based on a sum of each assigned adverse demerit increment value.

In some examples, determining the guideline demerit value includes obtaining treatment guideline ratings each assigned by the patient that measures a subjective level of importance to the patient for a corresponding treatment guideline, obtaining scaled guideline values for the corresponding available ADM based on the prescribing drug information and the published guidelines where each scaled guideline value is associated with a corresponding treatment guideline rating, and, for each treatment guideline rating, multiplying the treatment guideline rating times the corresponding scaled guideline value and a guideline demerit increment value. In these examples, the treatment guideline ratings include at least one of a cost rating, a body weight rating, a treatment regimen complexity rating, a treatment efficacy rating, a mealtime coverage needs rating, or a hypoglycemia rating.

For each of the available ADMs, the method may also include determining, by the data processing hardware, whether the patient is currently taking the corresponding available ADM based on the patient information, wherein the patient information includes a list of medications the patient is currently taking. When the patient is currently taking the corresponding available ADM, the method may further include assigning, by the data processing hardware, a low modified demerit value to the corresponding available ADM and adding, by the data processing hardware, the corresponding available ADM having the low modified demerit value to the predetermined number of recommended ADMs.

In some examples, for each of the available ADMs, the method further includes obtaining, by the data processing hardware, a list of excluded ADMs that the patient is either allergic to or is excluded from the treatment regimen for the patient and determining, by the data processing hardware, whether the corresponding available ADM is on the list of excluded ADMs. In these examples, when the corresponding available ADM is on the list of excluded ADMs, the method includes assigning, by the data processing hardware, a high modified demerit value to the corresponding available ADM and replacing, by the data processing hardware, the total demerit value for the corresponding available ADM with the assigned high modified demerit value.

In some implementations, the therapy regimen, when received by the patient device, causes the patient device to display the recommended ADMs and the recommended dosage for each recommended ADM on a patient interface executing on the patient device.

Additionally or alternatively, the method may also include transmitting the recommended dosage for at least one of the recommended ADMs to an administration device associated with the recommended ADM and in communication with the data processing hardware. Here, the administration device includes a doser and an administration computing device in communication with the doser. The administration computing device may be configured to cause the doser to administer the recommended dosage to the patient. In some examples, the administration device includes a smart pill bottle and the doser includes a locking/dispensing mechanism configured dispense one or more ADM pills based on the recommended dosage. In other examples, the administration device includes a smart pen that includes a cartridge containing the recommended ADM, and the doser includes a needle for insertion into the patient for administering the recommended ADM to the patient via the cartridge.

Another aspect of the disclosure provides a system for determining a therapy regimen. The system includes a patient device associated with a patient and a dosing controller in communication with the patient device. The dosing controller includes data processing hardware and memory hardware in communication with the data processing hardware. The dosing controller is configured to perform operations that include obtaining prescribing drug information and published guidelines for each of a plurality of Anti-Diabetes Medications (ADMs) available for managing glucose levels and receiving patient information from the patient device. The patient information is associated with the patient seeking selection and dosing of one or more of the available ADMs. For each of the available ADMs, the operations further include: determining an adverse demerit value, a guideline demerit value, and an instruction demerit value based on the patient information, the prescribing drug information, and published guidelines for the corresponding available ADM; and determining a total demerit value by summing the adverse demerit value, the guideline demerit value, and the instruction demerit value. The operations also include: ordering the total demerit values for the available ADMs from lowest to highest; selecting a predetermined number of recommended ADMs associated with the lowest total demerit values from the plurality of available ADMs; determining a recommended dosage for each recommended ADM based on the patient information, the prescribing drug information, and the published guidelines; and transmitting the therapy regimen from the data processing hardware to the patient device. The therapy regimen includes the recommended ADMs and the recommended dosage for each recommended ADM.

Implementations of the disclosure may include one or more of the following optional features. In some implementations, the patient information includes at least one of treatment preference information, treatment guideline ratings, a current medications list, current medical conditions associated with the patient, permanent medical conditions associated with the patient, one or more glucose values for the patient, or an A1c value for the patient. The treatment preference information includes at least one of a target glucose range for the patient, a target A1c value for the patient, a preferred minimum monthly treatment cost, or a preferred maximum monthly treatment cost. The treatment guideline ratings are each assigned by the patient and measure a subjective level of importance to the patient for a corresponding treatment guideline. The treatment guideline ratings include at least one of a cost rating, a body weight rating, a treatment regimen complexity rating, a treatment efficacy rating, a mealtime coverage needs rating, or a hypoglycemia rating. The current medications list includes a list of medications and corresponding dosages the patient is currently prescribed. The one or more glucose values for the patient are measured by a glucometer or a continuous glucose monitor in communication with the data processing hardware.

In some implementations, the operations further include receiving exercise data from a fitness tracker associated with the patient and adjusting the recommended dosage for at least one of the recommended ADMs based on the received exercise data. In some examples, determining the adverse demerit value includes obtaining one or more contraindicating conditions associated with the corresponding available ADM based on the prescribing drug information and the published guidelines, obtaining a list of medications that interact with the corresponding available ADM based on the prescribing drug information, and determining whether the patient currently has any of the contraindicating conditions associated with the corresponding available ADM based on the patient information that includes lab results associated with the patient. In these examples, determining the adverse demerit value further includes determining whether the patient is currently taking at least one of the medications that interact with the corresponding available ADM based on the patient information that includes a list of medications the patient is currently taking, assigning an adverse demerit increment value when the patient currently has any of the contraindicating conditions associated with the corresponding available ADM, assigning the adverse demerit increment value when the patient is currently taking at least one of the medications that interact with the corresponding available ADM, and determining the adverse demerit value for the corresponding available ADM based on a sum of each assigned adverse demerit increment value.

In some implementations, determining the guideline demerit value includes obtaining treatment guideline ratings each assigned by the patient that measures a subjective level of importance to the patient for a corresponding treatment guideline, obtaining scaled guideline values for the corresponding available ADM based on the prescribing drug information and the published guidelines where each scaled guideline value is associated with a corresponding treatment guideline rating, and, for each treatment guideline rating, multiplying the treatment guideline rating times the corresponding scaled guideline value and a guideline demerit increment value. In these implementations, the treatment guideline ratings includes at least one of a cost rating, a body weight rating, a treatment regimen complexity rating, a treatment efficacy rating, a mealtime coverage needs rating, or a hypoglycemia rating.

For each of the available ADMs, the operations may further include determining whether the patient is currently taking the corresponding available ADM based on the patient information, wherein the patient information includes a list of medications the patient is currently taking. When the patient is currently taking the corresponding available ADM, the operations may also include assigning a low modified demerit value to the corresponding available ADM and adding the corresponding available ADM having the low modified demerit value to the predetermined number of recommended ADMs.

In some implementations, for each of the available ADMs, the operations also include obtaining a list of excluded ADMs that the patient is either allergic to or is excluded from the treatment regimen for the patient and determining whether the corresponding available ADM is on the list of excluded ADMs. In these implementations, when the corresponding available ADM is on the list of excluded ADMs, the operations also include assigning a high modified demerit value to the corresponding available ADM and replacing the total demerit value for the corresponding available ADM with the assigned high modified demerit value.

In some examples, the therapy regimen when received by the patient device causes the patient device to display the recommended ADMs and the recommended dosage for each recommended ADM on a patient interface executing on the patient device. In some implementations, the operations also include transmitting the recommended dosage for at least one of the recommended ADMs to an administration device associated with the recommended ADM and in communication with the data processing hardware. Here, the administration device includes a doser and an administration computing device in communication with the doser. The administration computing device is configured to cause the doser to administer the recommended dosage to the patient. In some examples, the administration device includes a smart pill bottle and the doser includes a locking/dispensing mechanism configured dispense one or more ADM pills based on the recommended dosage. In other examples, the administration device includes a smart pen that includes a cartridge containing the recommended ADM and the doser includes a needle for insertion into the patient for administering the recommended ADM to the patient via the cartridge.

DESCRIPTION OF DRAWINGS

FIG. 3A is a schematic view of an example patient data table including a schedule of all patients treated by a respective Health Care Provider (HCP).

FIG. 3B is a schematic view of a permanent condition table for a respective patient including a list of permanent medical conditions associated with the patient.

FIG. 4A is a schematic view of a patient preferences table listing treatment preferences associated with a patient.

FIG. 4B is a schematic view of an allergies and exclusions table including a list of one or more ADMs that a patient is allergic to or that have been excluded from a treatment regimen for the patient.

FIG. 4C is a schematic view of a current medications table including a list of medications a patient is currently taking.

FIG. 4D is a schematic view of a patient device calibration table listing patient devices associated with a patient and calibration parameters associated with each patient device.

FIG. 4E is a schematic view of a patient device table including health data and exercise data obtained from one or more patient devices associated with the data.

FIG. 4F is a schematic view of a current conditions table including a list of conditions associated with lab test results for a patient.

FIG. 4G is a schematic view of a current labs table including a record of lab results for a patient.

FIG. 5A is a schematic view of an ADM table including a list of ADMs and pertinent information for each ADM.

FIG. 5B is a schematic view of a drug interactions table including a list of drugs/medications that interact with one of the ADMs from the ADM table of FIG. 5A.

FIG. 5C is a schematic view of an available dosages table for one of the ADMs from the ADM table of FIG. 5A.

FIG. 5E is a schematic view of a contraindications table including a list of contraindications associated with ADMs.

FIG. 5F is a schematic view of a guideline refreshment conversion process table including a list of guideline values assigned by a patient.

FIG. 5G is a schematic view of a configurable constants table.

FIG. 6B is a schematic view of an allergies and conditions screen indicating ADMs a patient is allergic to.

FIG. 6C is a schematic view of an energy-based dose adjustment screen for adjusting ADM dosages based on exercise.

FIG. 6D is a schematic view of an ADM selection screen displaying a treatment regimen for a patient that includes a list of recommended ADMs and recommended dosages for each recommended ADM.

FIG. 8 is a schematic view of an ADM selection table including a list of available ADMs.

Like reference symbols in the various drawings indicate like elements.

DETAILED DESCRIPTION

Diabetic outpatients affected by type 2 diabetes may maintain their glucose levels within desired ranges by using various combinations of therapies that includes injection dosages of insulin, dietary and exercise management, and anti-diabetes medications (ADMs). However, a wide variety of ADMs are available for treating type 2 diabetes, each of which may be associated with various characteristics. Therefore, it is desirable to have a clinical support system 100 (FIGS. 1A and 1B) that advises and manages selection and administration of ADMs.

Figure 1A:
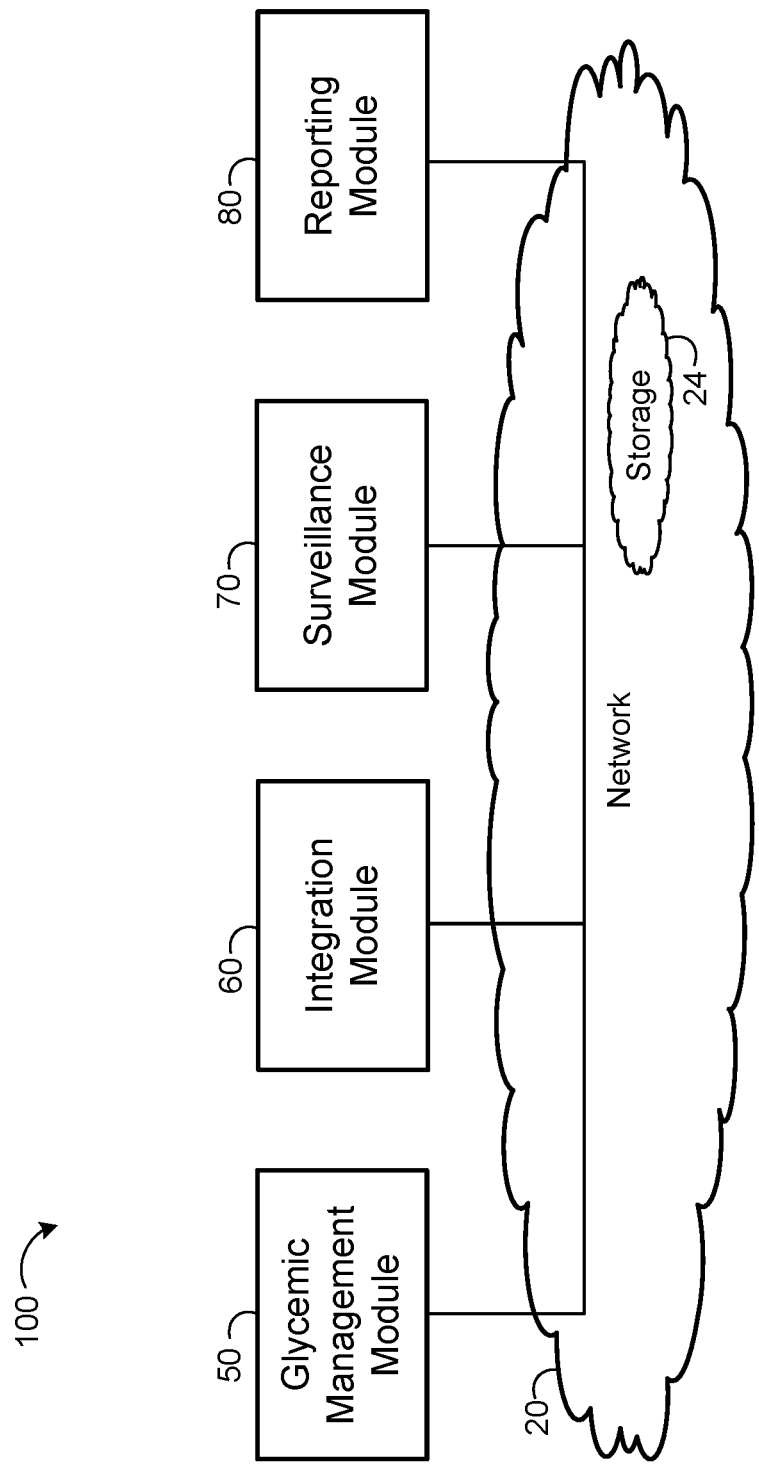
FIG. 1A is a schematic view of an example system for managing glucose levels of a patient.
Figure 1B:
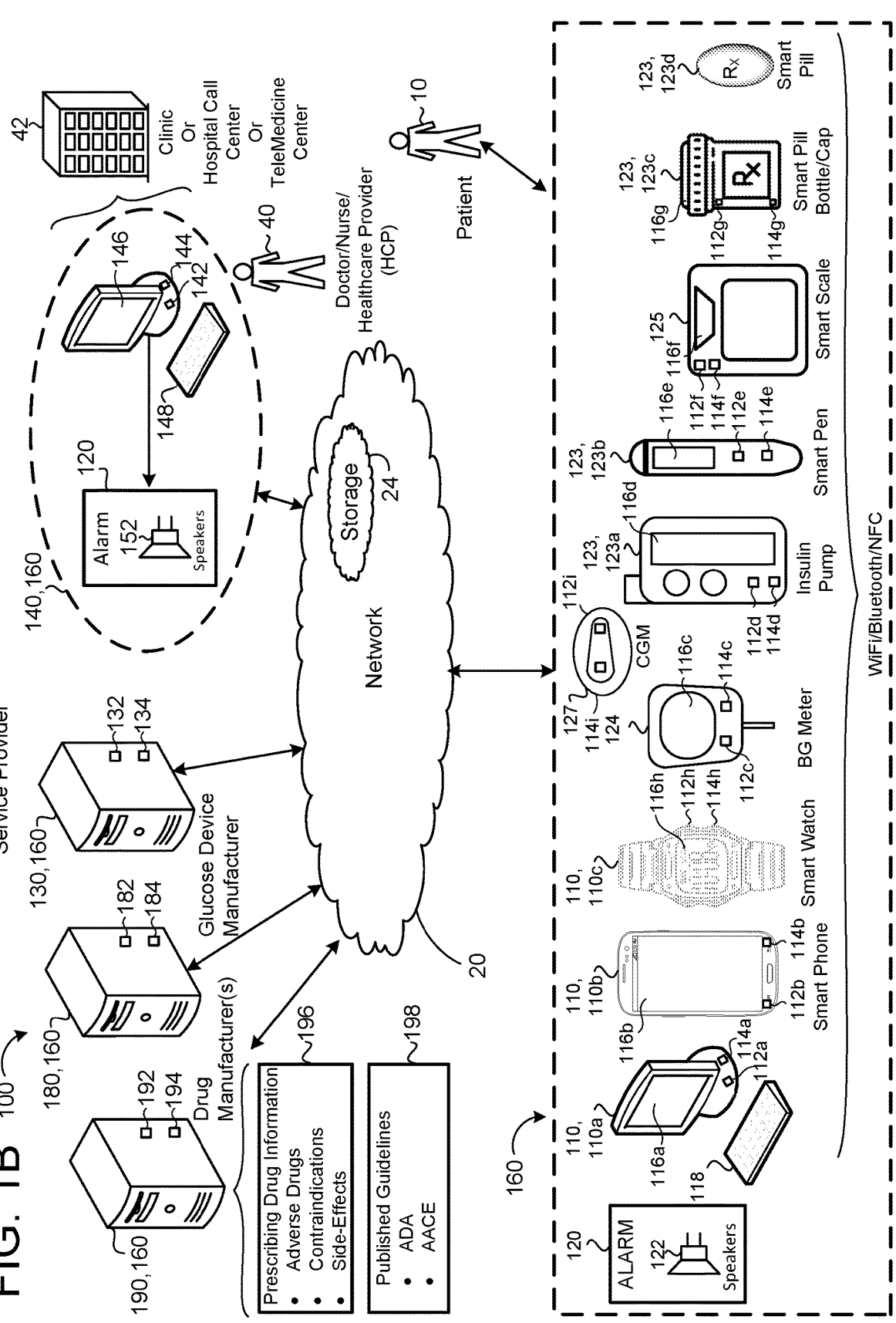
FIG. 1B is a schematic view of an example system for managing glucose levels of a patient.

Referring to FIGS. 1A and 1B, in some implementations, a clinical support system 100 analyzes inputted patient condition parameters for an outpatient 10 and selects and manages a personalized treatment regimen to adjust and maintain a glucose level or target A1C of the outpatient 10 within a target range. As used herein, the patient 10 refers to an outpatient that may be located at some remote location, such as the patient's 10 residence or place of employment. As used herein, the term "clinic" or "clinical" may refer to a location in which care managers provide healthcare services to patients. The system 100 includes a first program implemented in connection with one or more of: a personal computer 110, 110a of a patient 10; a patient device 110, 110b (e.g., mobile phone, tablet); a smart wearable 110, 110c (e.g., smart watch, fitness tracker); an insulin pump 123, 123a; a smart pen 123, 123b; smart pill bottle 123c; a smart pill 123d configured to detect and communicate ingestion; glucose meter (commonly referred to as "glucometer") 124; continuous glucose monitor (CGM) 127; a body weight scale 125, a service provider or health care professional (HCP) device 140; and/or a service provider 130. The glucose meter 124 and CGM 127 may be collectively referred to as a glucose measurement device 124, 127.

The system 100 further includes a second program, or dosing controller 160, that may reside in one or more of the patient device 110, the service provider device 140, and or the service provider 130. The dosing controller 160 provides advice on the selection and dosing of Anti-Diabetes Medications (ADMs). The dosing controller 160 may also advise and/or select dosing for insulin injections to manage the patient's 10 glucose values. Selection and dosing advice is determined by comparing a health status of the patient 10 to prescribing drug information 196 and published guidelines 198. The health status incudes: real-time data transmitted by the patient device(s) 110, 123, 124, 125, 127; digital downloads from the patient device(s) 110, 123, 124, 125, 127; laboratory tests; and judgement-based assessments by the HCP 40 and the patient 10. The prescribing drug information 196 and published guidelines 198 may be from published advisory literature including, but not be limited to, two types: 1) the Food and Drug Administration (FDA) approved labeling provided by the manufacturer of the ADM as a package insert, and 2) guidelines published by advisory institutions such as the American Diabetes Association (ADA) and the American Association of Clinical Endocrinologists (AACE).

The comparison of the health status to the aforementioned references 196, 198 is accomplished by the dosing controller 160, which then provides an output corresponding to selection and dosing of a treatment regimen. The results are used to improve glycemic control of the patient 10 by adjusting the selection and dosing of the ADMs. Selection and dosing may be controlled automatically by the dosing controller 160, or may include communicating information to the patient 10 in real-time so that he/she can manually change his/her ADM regimen.

In addition to selecting and managing ADMs, the dosing controller 160 may advise or prescribe changes in a dietary and exercise regimen of the patient 10. This is accomplished by calculating a net-energy budget that compares grams of carbohydrate consumed and calories of energy burned by regimented exercise and in the process of normal living. An excess or deficit of caloric energy would cause an increase or decrease in the Hemoglobin A1c of the patient 10, which is monitored as an indicator. The HCP 40 can prescribe changes in diet and exercise that will adjust the A1c of the patient 10 toward a target range.

Referring to FIGS. 1A and 1B, the clinical support system 100 includes a glycemic management module 50, an integration module 60, a surveillance module 70, and a reporting module 80. Each module 50, 60, 70, 80 is in communication with the other modules 50, 60, 70, 80 via a network 20. In some examples, the network 20 (discussed below) provides access to cloud computing resources that allows for the performance of services on remote devices instead of the specific modules 50, 60, 70, 80. The glycemic management module 50 executes the program 160 (e.g., an executable instruction set) on a computing device 112, 132, 142 or on the cloud computing resources. The integration module 60 allows for the interaction of users 40 and patients 10 with the system 100. The integration module 60 receives information inputted by a user 40 and allows the user 40 to retrieve previously inputted information stored on a storage system (e.g., one or more of cloud storage resources 24, a non-transitory memory 144 of an electronic medical system 140 of a clinic 42 or telemedicine facility, a non-transitory memory 114 of the patient device 110, a non-transitory memory 134 of the service provider's system 130, or other non-transitory storage media in communication with the integration module 60). The storage resources 24 and non-transitory memory 114, 134, 144 may individually or collectively be referred to as memory hardware. Therefore, the integration module 60 allows for the interaction between the HCPs 40, patients 10, and the system 100 via a display 116, 146. The surveillance module 70 considers patient information received from a HCP 40 via the integration module 60 and information received from a glucometer 124 or CGM 127 that measures a patient's glucose value and determines if the patient 10 is within a threshold glucose value. Generally, the glucometer 124 measures capillary "blood glucose" values and the CGM 127 measures "interstitial glucose" values that can be correlated to blood glucose values. As used herein, the term "glucose value" refers to either one of blood glucose or interstitial glucose. Moreover, use of the term "blood glucose" is not meant to imply that the CGM 127 was not used due to the correlation between interstitial glucose and blood glucose. In some examples, the surveillance module 70 alerts the user 40 if a patient's glucose values are not within a threshold glucose value. The surveillance module 70 may be preconfigured to alert the user 40 of other discrepancies between expected values and actual values based on pre-configured parameters. For example, when a patient's glucose value drops below a lower limit of the threshold glucose value. The reporting module 80 may be in communication with at least one display 116, 146 and provides information to the user 40 determined using the glycemic management module 50, the integration module 60, and/or the surveillance module 70. In some examples, the reporting module 80 provides a report that may be displayed on a display 116, 146 and/or is capable of being printed.

The system 100 is configured to evaluate a glucose level, a nutritional intake, and lifestyle of a patient 10. Based on the evaluation and analysis of the data, the system 100 selects and executes a treatment regimen, which is administered to the patient 10 to adjust and maintain the glucose value of the patient 10 into a glucose target range. The system 100 may be applied to various devices, including, but not limited to, patient devices 110, subcutaneous insulin infusion pumps 123a, smart pens 123b, smart pill bottles 123c, smart pills 123d, glucometers 124, CGM 127, and smart scales 125. Smart pens 123b may include ADM pens for injecting ADMs to the patient subcutaneously or may include insulin pens for injecting insulin to the patient 10 subcutaneously.

In some examples, the clinical support system 100 includes the network 20, the patient device 110, the dosing controller 160, a service provider 130, and a glucose device manufacturer provider 180. The patient device 110 may include, but is not limited to, desktop computers 110a or portable electronic device 110b (e.g., cellular phone, smartphone, personal digital assistant, barcode reader, personal computer, or a wireless pad), activity trackers 110c (e.g., smart watch, fitness band) or any other electronic device capable of sending and receiving information via the network 20. In some implementations, one or more of the patient's glucometer 124, CGM 127, insulin pump 123a, pen 123b, or bottle/cap 123c are capable of sending and receiving information via the network 20.

The patient device 110a, 110b, 110c includes a data processor 112a, 112b, 112h (e.g., a computing device that executes instructions), non-transitory memory 114a, 114b, 114h and a display 116a, 116b, 116h (e.g., touch display or non-touch display) in communication with the data processor 112a, 112b, 112h. In some examples, the patient device 110 includes a keyboard 118, speakers 122, microphones, mouse, and a camera.

The insulin pump 123a, pen 123b, glucometer 124, and CGM 127 associated with the patient 10 may include a data processor 112c, 112d, 112e, 112i (e.g., a computing device that executes instructions), and non-transitory memory 114c, 114d, 114e, 114i, and/or a display 116c, 116d, 116e (e.g., touch display or non-touch display) in communication with the data processor 112c, 112d, 112e, 112i. The devices 123a, 123b, 124, 127 may also communicate wirelessly through the network 20 and/or with any other patient device 110, 123a, 123b, 123c, 124, 125, 127 through the same or different network 20.

The smart scale 125 and the smart bottle 123c each include a data processor 112f, 112g, (e.g., a computing device that executes instructions). The smart scale 125 and the smart bottle 123c further include non-transitory memory 114f, 114g and a display 116f, 116g (e.g., touch display or non-touch display) in communication with the data processor 112f, 112g.

The clinical support system 100 may also include a glucose device manufacturer provider 180 including a data processor 182 in communication with non-transitory memory 194. The data processor 192 may execute a proprietary download program for downloading glucose data from the memory 114c of the patient's glucometer 124 and/or from the memory 114i of the patient's CGM 127. In some implementations, the heal care provider 140 implements the proprietary download program on a computing device 142 or the proprietary download program is implemented on the patient device 110 for downloading the glucose data from the memory 114c. In some examples, the download program exports a glucose data file for storage in the non-transitory memory 24, 114, 144. The data processor 182 may execute a web-based application for receiving and formatting glucose data transmitted from one or more patient devices 110a, 110b, 124, 123a, 123b, 123c, 127 and storing the glucose data in non-transitory memory 24, 114, 144.

The drug manufacturer provider 190 may include a data processor 192 in communication with non-transitory memory 194. The memory 194 may store the prescribing drug information 196 and the published guidelines 198, and the data processor 192 may provide the prescribing drug information 196 and the published guidelines 198 to the dosing controller 160 for outputting a corresponding selection and dosing of a treatment regimen for the patient 10 based on the health status of the patient 10.

The services provider 130 may include a data processor 132 in communication with non-transitory memory 134. The service provider 130 provides the patient 10 with a program 162 (see FIG. 1D) (e.g., a mobile application, a web-site application, or a downloadable program that includes a set of instructions) executable on a computing device 112, 132, 142 of the dosing controller 160 and accessible through the network 20 via the patient device 110, health care provider electronic medical record systems 140, portable glucose measurement devices 124, 127 (e.g., glucose meter, glucometer, or CGM), or portable administration devices 123a, 123b, 123c.

Figure 2:
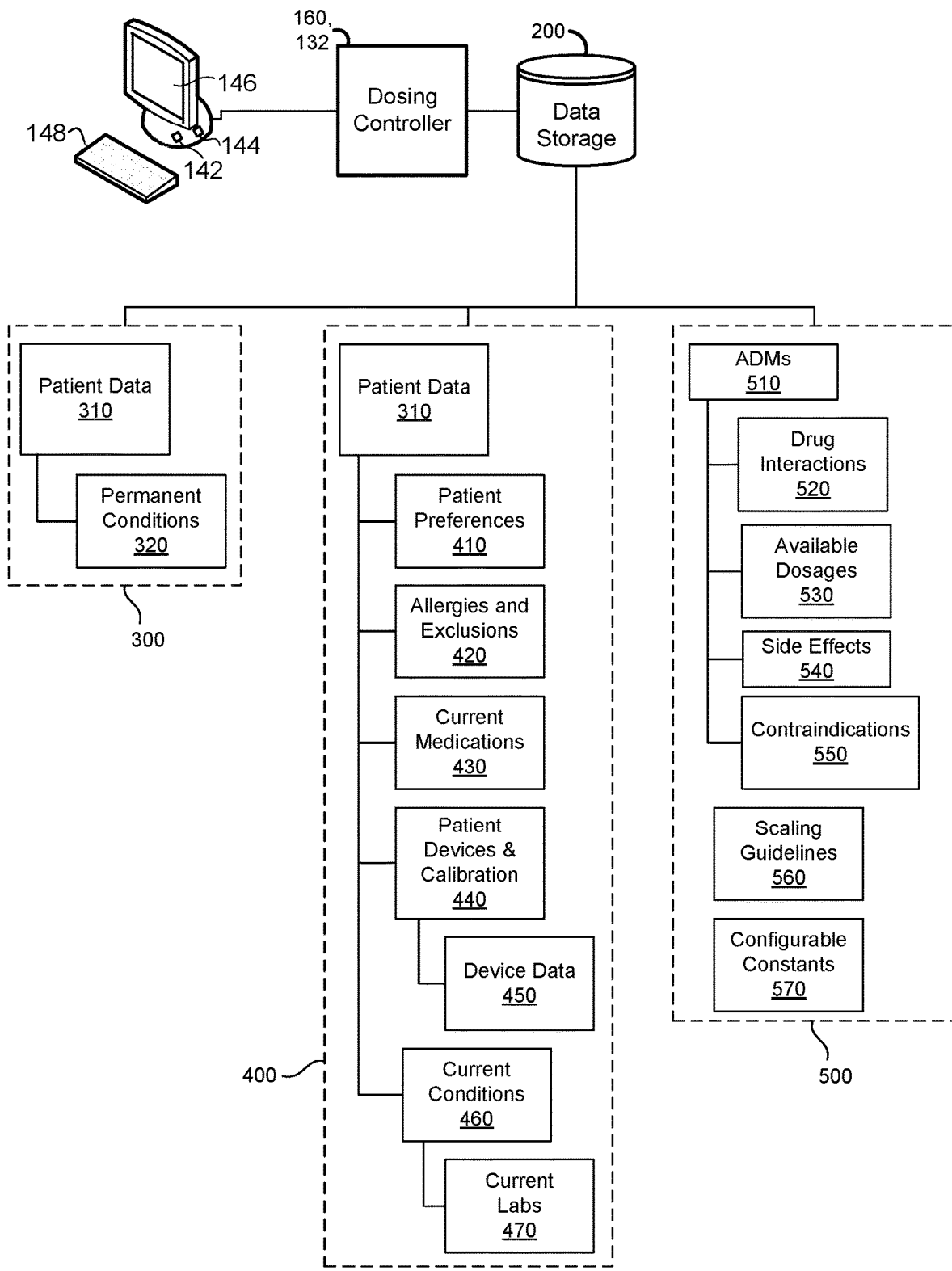
FIG. 2 is a schematic view of an example dosing controller configured to execute instructions to evaluate and select Anti-Diabetes Medications (ADMs) to be included in a treatment regimen for a patient.

In some implementations, the HCP medical record system 140 is located at a doctor's office, clinic 42, or a facility administered by a hospital (such as a hospital call center) and includes a data processor 142, a non-transitory memory 144, and a display 146 (e.g., touch display or non-touch display). The non-transitory memory 144 and the display 146 are in communication with the data processor 142. In some examples, the HCP electronic medical system 140 includes a keyboard 148 in communication with the data processor 142 to allow a user 40 to input data, such as fixed patient data 300 (FIG. 2). The non-transitory memory 144 maintains patient records capable of being retrieved, viewed, and, in some examples, modified and updated by authorized hospital personal on the display 146.

The dosing controller 160 is in communication with the glucose measurement devices 124, 127 and the administration devices 123, and includes a computing device 112, 132, 142 and non-transitory memory 114, 134, 144 in communication with the computing device 112, 132, 142. The dosing controller 160 executes the program 162. The dosing controller 160 stores patient related information retrieved from the glucose measurement devices 124, 127, patient devices 110, and/or smart scale 125 to determine ADM selections and dosing parameters (and insulin dosing parameters in some scenarios) based on the received glucose measurement and other factors associated with the patient 10, such as activity level, weight, and/or meal consumption.

Figure 1C:
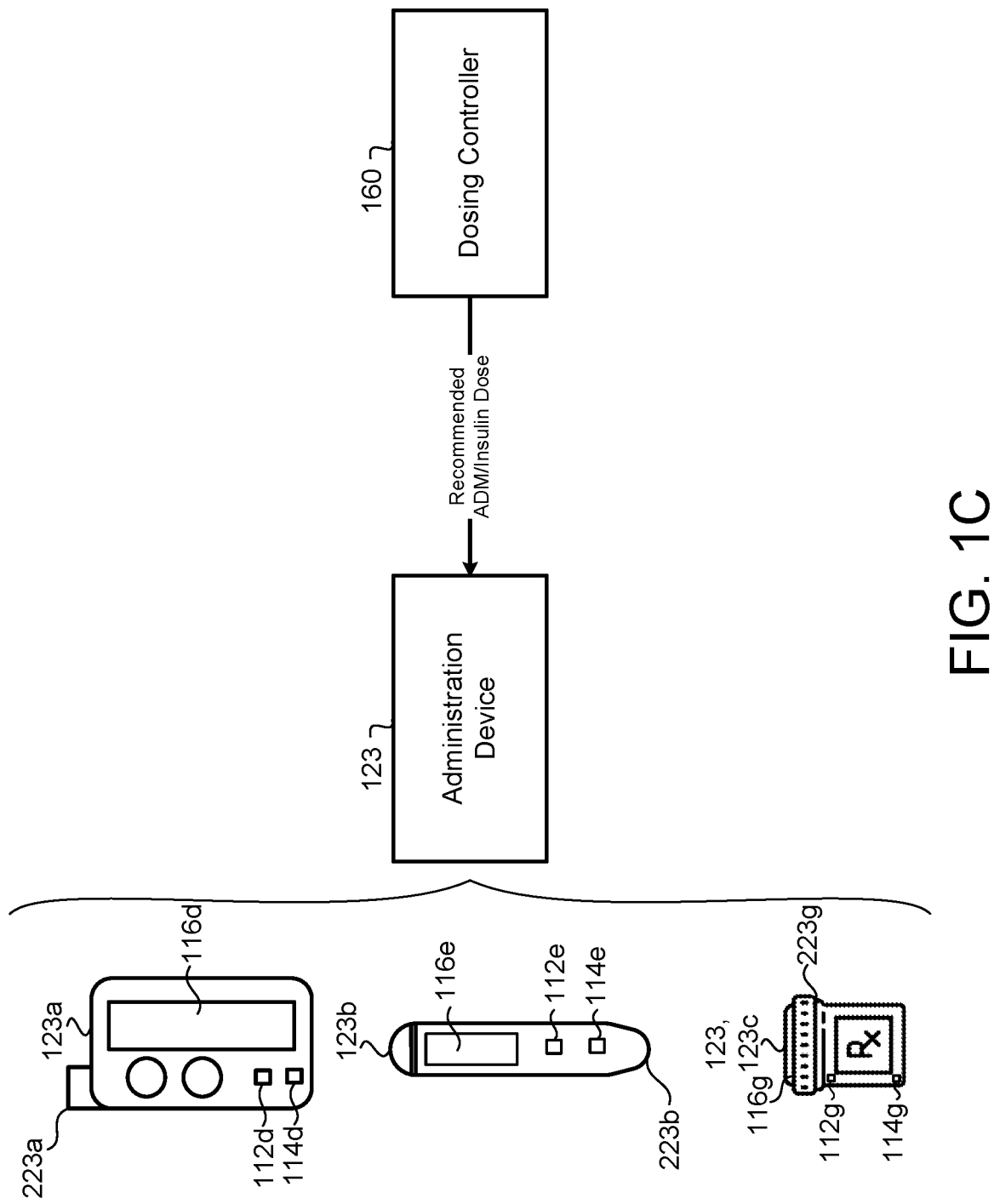
FIG. 1C is a schematic view of an example administration device in communication with a dosing controller.

Referring to FIG. 1C, in some implementations, the administration device 123 (e.g., insulin pen, smart pill bottle/cap, smart pill), in communication with the dosing controller 160, is capable of executing instructions for administering insulin and/or ADM(s) according to an anti-diabetes treatment regimen selected by the dosing controller 160. The administration device 123 may include the insulin pump 123a, the pen 123b, or the smart pill bottle/cap 123c. The administration device 123 is in communication with the patient devices 110, the glucometer 124, the CGM 127, and the smart scale 125 and includes a computing device 112d, 112e, 112g and non-transitory memory 114d, 114e, 114g in communication with the computing device 112d, 112e, 112g. The administration device 123 includes a doser 223a, 223b, 223g in communication with the administration computing device 112d, 112e, 112g for administering an ADM or insulin to the patient 10. For instance, the doser 223a of the insulin pump 123a includes an infusion set including a tube in fluid communication with an insulin reservoir and a cannula inserted into the patient's 10 body and secured via an adhesive patch. The doser 223b of the pen 123b of the pen 123b includes a needle for insertion into the patient 10 for administering an ADM or insulin to the patient via a cartridge. The doser 223g of the smart pill bottle/cap 123c may include a locking mechanism that unlocks the bottle 123c for administering an ADM pill by the patient 10. Additionally or alternatively, the doser 223g may include a dispensing mechanism that dispenses one or more ADM pills for administering to the patient 10. In some examples, the doser 223g communicates with the display 116g and/or speaker for presenting a visual and/or audio alert to notify the patient 10 it is time to administer a specified dosage of one or more ADM pills. The administration device 123 is in communication with the dosing controller 160, and receives instructions from the dosing controller relating to administration of recommended dosages of insulin or ADMs. Here, the administration computing device 112d, 112e, 112g may execute the anti-diabetes treatment regimen selected by the dosing controller 160 and need not be pre-programmed to execute various anti-diabetes treatment regimens/programs stored within memory 114d, 114e, 114g, thereby reducing memory usage while increasing processing speeds thereof. Thus, executing the anti-diabetes treatment regimen by administration computing device 112d, 112e, 112g causes the doser 223a, 223b, 223b to administer doses of ADMs or insulin specifically tailored for the patient 10 as specified by the anti-diabetes treatment regimen. Accordingly, the administration devices 123a, 123b, 123c may be "smart" administration devices capable of communicating with the dosing controller 160 to populate recommended doses of ADMs or insulin for administering to the patient 10. In some examples, the administration devices 123a, 123b, 123c execute the dosing controller 160 on the administration computing devices 112d, 112e, 112g to calculate the recommended doses of ADMs or insulin for administering to the patient 10.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, Long-Term Evolution (LTE) network, fifth generation (5G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

Figure 1D:
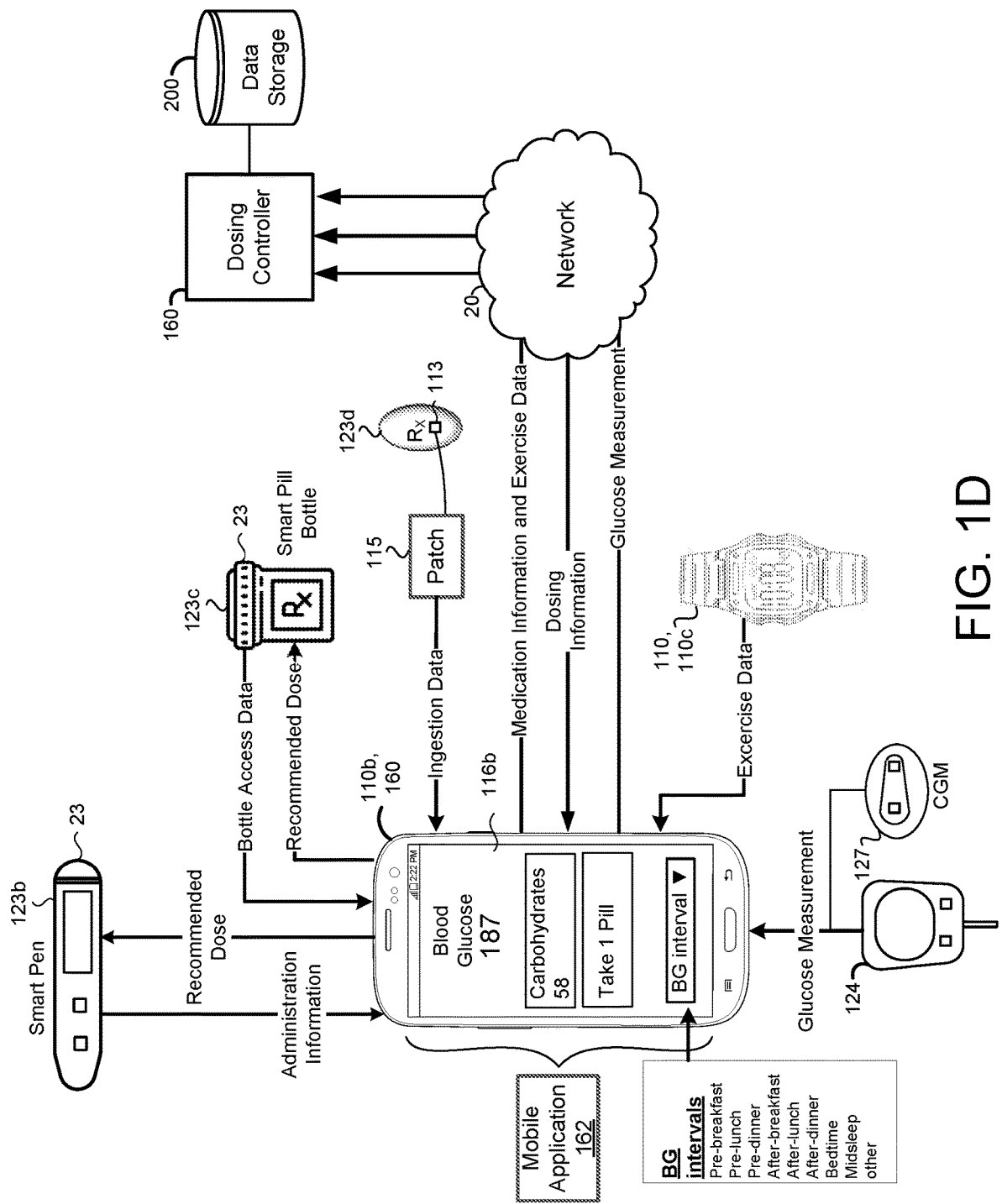
FIG. 1D is a schematic view of example components of the system of FIGS. 1A-1C.

FIG. 1D is a schematic view of exemplary components of the system 100. In some implementations, the administration device 123 associated with the patient 10 includes a smart pen 123b or smart pill bottle 123c that is capable of communicating (e.g., syncing) with a patient device 110 such as a smart phone 110b. In the example shown, the smart pen 123b and smart pill bottle 123c communicate with the smart phone 110b via Bluetooth, however, other wireless or wired communications are possible. The smart pen 123b and/or smart pill bottle 123c may include an associated smart cap 23 that removably attaches to the respective smart pen 123b or smart pill bottle 123c. For instance, the smart cap 23 may attach to the smart pen 123b to enclose and protect the doser 223b when not being used to administer the ADM or insulin, and then removed from the pen 123b to expose the doser 223b when the patient 10 is administering and ADM or insulin. Similarly, the smart cap 23 may attach to the smart pill bottle 123c to enclose/seal the ADM pills within the smart pill bottle 123c and be removed to provide access to the bottle when the patient 10 is administering one or more ADM pills. In some implementations, the smart cap 23 implements some or all of the functionality of the respective smart pen 123b or smart pill bottle 123c. For instance, the smart cap 23 may include the processor 112e, 112g, the non-transitory memory 114e, 114g and/or the display 116e, 116g instead of the smart pen and smart pill bottle 123b, 123c, or the pen 123b and/or bottle 123c may each implement at least one of the processor 112e, 112g the non-transitory memory 114e, 114g and/or the display 116e, 116g. Accordingly, the smart cap 23 may communicate with the patient device 110 (e.g., smart phone 110b) via Bluetooth or through other wireless or wired communications.

In some configurations, the fitness tracker 110c communicates exercise data to the smart phone 110b via Bluetooth, infrared, cable, or other communications. The mobile application (e.g., program) 162 may execute on the computing device 112b of the smart phone 110b to provide the exercise data to the dosing controller 160. The exercise data may include, without limitation, calories burned, walking steps, running steps, miles run, miles walked, and resistance repetitions. The dosing controller 160 may use exercise data when determining a recommended dose of an ADM or insulin for the patient to administer. The patient 10 may additionally or alternatively input the exercise data into the smart phone 110b or other device in communication with the smart phone 110b.

The glucometer 124 and CGM 127 may also communicate glucose measurements to the smart phone 110b via Bluetooth, infrared, cable, or other communications. The mobile application 1198 executing on the computing device 112b of the smart phone for communicating with the dosing controller 160 such that information can be communicated over the network 20 between the dosing controller 160 and each of the smart pill bottle 123c (and/or cap 23), smart pen 123b (and/or cap 23), the glucometer 124, the CGM 127, and the fitness tracker 110c. For example, dosing parameters (dosing information) adjusted by the dosing controller 160 may be transmitted to the smart phone 110b and stored within memory 114b (FIG. 1B). The dosing parameters may include, but are not limited to: TargetBG; target A1c, recommended basal/bolus doses of insulin; recommended ADM doses and types; and scheduled administration times for administering doses of ADMs or insulin. The dosing parameters may be adjusted automatically or manually initiated by the user/HCP 40 or patient 10.

In some implementations, upon the glucometer 124 or CGM 127 determining a glucose measurement, the glucometer 124 or CGM 127 transmits the glucose measurement to the smart phone 110b. The smart phone 110b may render the glucose measurement upon the display 116b and permit the patient 10 to select the BGtype associated with the glucose measurement. The BGtype or BG Interval corresponds to a label or tag chosen by the patient 10 from a dropdown list upon the display 116b of the smart phone 110b. Alternatively, the patient 10 may select the BG Interval from a dropdown list displayed on the display 116c of the glucometer. The smart phone 110b may transmit the glucose measurement and the BG type to the dosing controller 160 via the network 20. In some examples, the glucometer 124 or CGM 127 is configured to transmit the glucose measurement and/or BG type directly to the dosing controller 160 via the network 20. The patient 10 may also input meal information, such as carbohydrates consumed for breakfast, lunch, or dinner, to the smart phone 110b.

In some examples, the patient 10 may enter a number of carbohydrates for a current meal into the glucometer 124, the CGM 127, or fitness tracker 110c for transmission to the smart phone 110b or directly into the smart phone 110b when a glucose measurement is received. For instance, upon receiving the glucose measurement from the glucometer 124 or the CGM 127, the smart phone 110b may render an interactive graphic upon the display 116b that enables the patient to enter the number of carbohydrate grams the patient 10 plans to ingest. The mobile application 1198 executing on the smart phone 110b may provide the glucose measurement and the number of carbohydrate grams to the dosing controller 160 for calculating the recommended dose for display on the display 116b.

In some implementations, a recommended dose is determined by the dosing controller 160 and sent to the smart phone 110b during each adjustment transmission and stored within the memory 114b. The recommended dose may include one or more ADM pills or a dosage of insulin for the patient 10 to administer. Accordingly, upon receiving the recommended dose, the mobile application 1198 sends the appropriate number of ADM pills, doses of ADM, or doses of insulin to the smart pill bottle 123c or the smart pen 123b. In some examples, the smart pen 123b (using the administration computing device 112e) automatically dials in the total number of units for the recommended dose of ADM or insulin for the doser 223b to administer. The patient 10 may interact with the smart pen 123b (or cap 23) or smart pill bottle 123c (or cap 23) to accept the recommended dose displayed upon the display 116e or manually change the recommended dose. The doser 223b of the smart pen 123b may include an electro-mechanical stop that actuates a plunger to only administer the recommended dosage of ADM or insulin accepted by the patient 10 or dosage of ADM or insulin manually entered by the patient 10. Likewise, the doser 223g of the smart pill bottle 123c may include a locking mechanism that unlocks to dispense a number of ADM pills corresponding to the recommended dosage of ADM. In some examples, upon administration of an ADM or insulin dose by the administration device 123 (e.g., smart pen 123b or smart pill bottle 123c), the administration device 123 transmits the value of the administered dose (or bottle access data) and the time of the administered dose (or bottle access data) to the smart phone 110b for storage within memory 114b along with the associated BG measurement. Additionally, the smart phone 110b may transmit the administered dose (or bottle access data) and the time of the administered dose (or bottle access data) to the dosing controller 160 via the network 20. In some configurations, the smart pen 123b (or cap 23) and/or smart pill bottle 123c (or cap 23) forms a direct communication link with the dosing controller 160 via the network 20 for receiving the recommended dosing information and/or transmitting the administered dose and the time of the administered dose to the dosing controller 160.

In some implementations, an ADM pill includes the ADM smart pill 123d that includes the ADM as well as an ingestible sensor 113 that activates when in contact with stomach fluid to detect when the patient 10 administers the pill. Subsequently, the pill is configured to transmit activation by the sensor 113 to a wearable patch 115 (or other transceiver) that transmits the ingestion data to the smart phone 110b. The application 162 executing on the smart phone 110c may log the received ingestion data along with a corresponding time stamp to allow the HCP 40 to access the ingestion data to determine if the patient 10 is being compliant. The patch 115 may include an adhesive for attaching to the patient skin near the stomach, and a transceiver for receiving an indication that the ingestible sensor 113 has been activated upon ingestion and transmitting the ingestion data to the smart phone 110b or other patient device 110. In some examples, if ingestion data is not received by a time threshold for administering the ADM smart pill 123d, the dosing controller 160 may send an alert to the administration device 123 to remind the patient 10 to administer a recommended dosage of the ADM pill 123d in case the patient 10 forgot to administer the pill.

With reference to FIG. 2, the dosing controller 132, 160 is configured to execute instructions to evaluate and select ADMs to be included in a treatment regimen based on a plurality of linked tables maintained in data storage 200 of the memory 24, 114, 134, 144. Each of the tables can be classified into one of three categories: (i) fixed patient data 300; (ii) dynamic patient data 400; and (iii) reference data 500. Tables including fixed patient data 300 are shown in FIGS. 3A and 3B and contain data permanently associated with each individual patient 10, such as identification, demographics, and permanent medical information, for example. Tables including dynamic patient data 400 contain date-stamped data associated with dates-of-service and changes in the health status and therapy of the patient 10. Examples of tables including dynamic patient data 400 are shown in FIGS. 4A-4G. Tables including reference data 500 are applied universally throughout the system 100 for all patients 10. The tables including reference data 500 contain published information from third-party resources, and are periodically updated based on revisions by the third-party resource. Examples of tables including reference data 500 are shown in FIGS. 5A-5G.

Referring to FIG. 3A, a patient data table 310 of the fixed patient data 300 is provided and includes a schedule of all patients 10 treated by a respective HCP 40. The patient data table 310 is linked to a plurality of sub-tables 320, 410, 420, 430, 440, 450, 450, 470 in a few-to-many relationship, whereby data related to each record 312, 312a-c (i.e., patient) in the patient data table 310 is stored in each of the various sub-tables corresponding to the record. For example, the second record 312, 312b associated with Tilly Typical in the patient data table 310 of FIG. 3A may be linked to the permanent conditions table 320 shown in FIG. 3B. The permanent conditions table 320 includes a schedule of permanent conditions associated with patient Tilly Typical.

Referring back to FIG. 2, the patient data table 310 is further linked to a plurality of sub-tables including dynamic patient data 400. As shown in FIG. 4A, a patient preferences table 410 includes treatment preference information 411, 411a-d and treatment guideline ratings 412, 412a-f for a single one of the patients 10 in the patient data table 310. For example, the treatment preference information 411, 411a-d may include a target glucose (BG_Target) 411a, a target A1c (A1c_Target) 411b, a preferred minimum monthly treatment cost (ADM_$_perMo_Low) 411c, and a preferred maximum monthly treatment cost (ADM_$_perMo_Hi) 411d.

The treatment guideline ratings 412 of the patient preferences table 410 are associated with an importance of corresponding treatment guidelines. In the illustrated example, the treatment guideline ratings 412 include cost (Cost_Importance) 412a, effect on body weight (Weight_Importance) 412b, treatment regimen complexity (Complexity_Importance) 412c, treatment efficacy (Efficacy_Importance) 412d, mealtime coverage needs (Mealtime_Coverage_Importance) 412e, and risk of hypoglycemia (Hyopglycemia_Importance) 412f. Each treatment guideline rating (412) is assigned a numeric rating based on the patient's 10 subjective level of importance for the treatment guideline. In the illustrated example, the importance of the treatment guidelines are rated using a binary scale, whereby a rating of "0" corresponds to a treatment guideline having little or no importance to the patient, and a rating of "1" corresponds to a treatment guideline having high importance. In some implementations, importance of each treatment guideline is indicated based on a scaled rating. For example, importance may be indicated based on a scale from 1 to 10, with a value of "1" being associated with a lowest level of importance to the patient 10 and a value of "10" being associated with a highest level of importance to the patient 10.

The dosing controller 160 may periodically update the patient preferences table 410 based on feedback received from the patient 10. Here, the patient 10 may provide patient preference feedback to his/her healthcare provider(s) during office visits, phone consultations, or electronic communications, and the HCP 40 may provide the patient preference feedback to the dosing controller 160 to update the patient preferences table 410. For example, as shown in FIG. 4A, on Jun. 17, 2016 the HCP 40 with the surname Pepper updated the patient preferences table 410 to indicate that treatment cost 412a was now of high importance to the patient, and on Jun. 28, 2016 another HCP 40 with surname Livingston updated the patient preferences table 410 to indicate that effect on body weight 412b was of high importance to the patient 10.

Figure 6A:
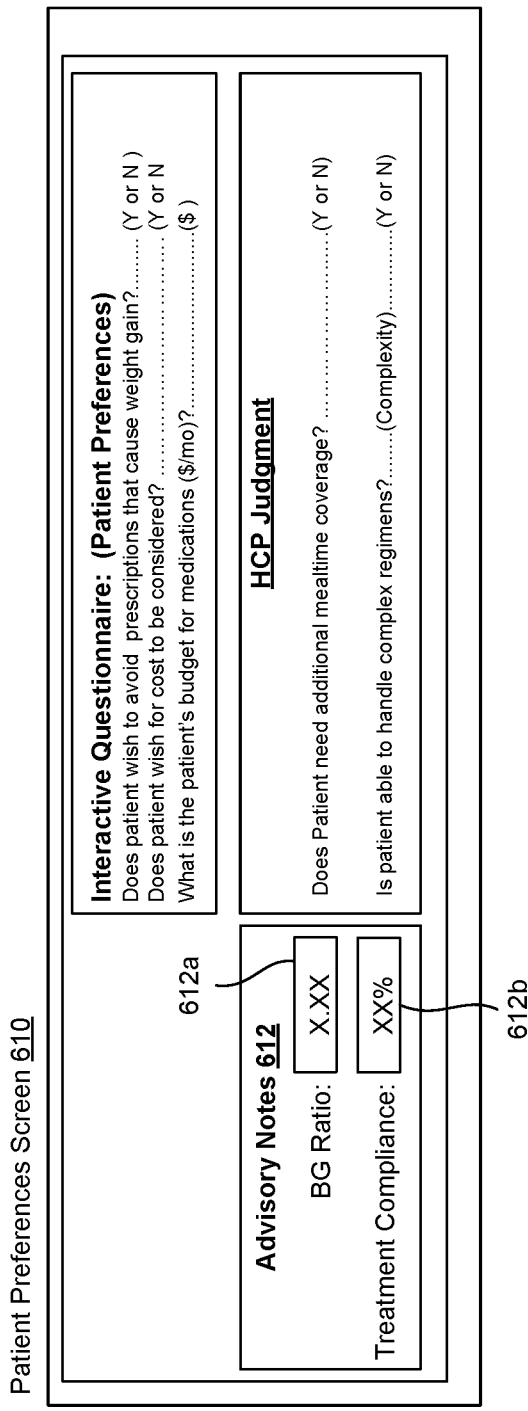
FIG. 6A is a schematic view of a patient preferences screen.

The patient preferences table 410 may be updated via an interactive patient preferences screen 610, as shown in FIG. 6A. The patient preferences screen 610 presents the HCP 40 or a patient 10 with a series of questions corresponding to the treatment guideline ratings 412. For example, the patient preferences screen 610 may present a first series of questions to be answered by the patient 10, including questions related to the importance of an effect on body weight guideline, the treatment cost guideline, and, if necessary, the minimum and maximum monthly treatment costs. The patient preferences screen 610 may also include questions to be answered by the HCP 40. For example, the interactive input may include questions relating to the HCP's judgment with respect to the requirement for additional mealtime coverage and the ability of the patient to handle a complex treatment regimen. As provided above, the responses to these questions are stored in the patient preferences table 410 as ratings 412 of 0 (i.e., "no") or 1 (i.e., "yes").

With continued reference to the patient preferences screen 610, the HCP may be presented with one or more advisory notes 612 including data relevant to determining and selecting treatment guideline ratings 412 for the patient. For example, the advisory notes 612 may include a first advisory note 612a displaying a calculated glucose (BG) ratio for consideration when determining whether the patient requires additional mealtime coverage. The BG ratio 612a is calculated by taking a mean of all BG measurements taken during lunch ($BG_{Lunch}$), dinner ($BG_{Dinner}$), and bedtime ($BG_{Bedtime}$) intervals, over a mean of all BG measurements taken during a fasting interval prior to breakfast ($BG_{Breakfast}$). For instance, the BG ratio 612a may be expressed by the following formula:

$$BG\ Ratio = \frac{\text{Average}\ (BG_{Lunch}, BG_{Dinner}, BG_{Bedtime})}{\text{Average}\ (BG_{Breakfast})} \qquad (1)$$

Additional concepts and features related to average BG measurements for each of the BG intervals can be found in U.S. Patent Application Publication No. 2017/0228518, the disclosure of which is incorporated herein in its entirety. A BG ratio 612a greater than 1.00 indicates that the average meal-related BG measurements ($BG_{Lunch}$, $BG_{Dinner}$, $BG_{Bedtime}$) are higher than the average fasting BG measurements taken before breakfast ($BG_{Breakfast}$). Conversely, for BG Ratios less than or equal to 1.00, the HCP may identify the patient as not requiring additional mealtime coverage. Accordingly, an advisory note showing the BG ratio 612a is provided to the HCP in the patient preferences input screen 610 so that the HCP may identify the patient as needing additional mealtime coverage.

Referring still to the patient preferences screen 610 of FIG. 6A, the HCP may also be presented with an advisory note 612 indicating a treatment compliance rate 612b for the patient 10, which can be considered by the HCP 40 in determining whether the patient 10 is capable of handling complex treatment regimens. The system calculates the treatment compliance rate based on information obtained from the patient device data table 450 shown in FIG. 4E. For example, as shown in FIG. 4E, the patient 10 may be associated with a smart pill bottle (eBottle_Rx) 123c capable of tracking each instance of the bottle 123c being opened (e.g., the bottle access data of FIG. 1D). The number of bottle openings (Bottle_Openings_wk) is then stored in the device data table 450. Treatment compliance rate 612, 612b is then calculated as a ratio of the number of measured bottled openings per week over the scheduled doses per week by the following formula:

$$\text{Treatment Compliance} = \frac{\text{Measured Bottle Openings}}{\text{Scheduled Doses}} \quad (2)$$

If more than one medication is currently prescribed to the patient 10, the treatment compliance rate 612, 612b may be calculated as an average of the treatment compliance rate for each one of the prescribed medications.

Referring to FIG. 4B, an allergies and exclusions table 420 includes a listing of all ADMs that a patient is either allergic to or that have been excluded from the treatment regimen for other reasons. For example, ADMs may be excluded by the patient 10 or HCP 40 based on the undesirable side-effects or contraindications. The allergies and exclusions table 420 is in reciprocal communication with an allergies and conditions screen 620 (FIG. 6B). Here, the data included in the allergies and exclusions table 420 is presented to the patient 10 or HCP 40 in the allergies and conditions screen 620 on the display 116, 146. The allergies and exclusions table 420 may update based on feedback received from inputs to the allergies and conditions screen 620 by the patient 10 or HCP 40. This interactive relationship is described in greater detail below.

FIG. 4C illustrates an example of a current medications table 430 including a listing of all medications currently being taken by the patient 10. The current medications table 430 may also be referred to as a current medications list 430. As shown in rows 2 and 3 of the illustrated current medications table 430, non-ADM medications may also be included in the current medications table 430. The current medications table 430 is queried by the program 160 as part of determining potentially adverse interactions between suggested treatment regimens and medications currently taken by the patient 10. Further, once a treatment regimen is selected and implemented, the ADM selection program 160 may update the current medications table 430 to include changes or additions to the listed medications.

Referring to FIGS. 2, 4D and 4E, the data storage 200 further includes a patient device calibration table 440 and the patient device data table 450 discussed above. The patient device data table 450 may be provided as a linked child (FIG. 2) to the patient device calibration table 440, whereby the patient device data table 450 is used by the system 100 to maintain calibration of each of the devices. For example, the patient may use a fitness tracker 110c, a smart phone 110b, a BG monitor 124, a smart pill bottle 123c, and a smart scale 125 all listed by the patient device calibration table 440 and the patient device data table 450. The data for each of the devices 110c, 110b, 124, 123c, 125 in the patient device data table 450 is communicated to the system 100 from each device 110c, 110b, 124, 123c, 125. Accordingly, the patient device data table 450 may be updated in real-time, at regular intervals, or on-demand.

Based on the data provided in the patient device data table 450, each of the devices 110c, 110b, 124, 123c, 125 can be calibrated. For example, the parameter of Calories-per-Mile-by-GPS can be calibrated by taking the actual calories burned by GPS for the previous week divided by the actual miles by GPS for the previous week. For instance, the Calories-per-Mile-by-GPS can be calculated by the following formula:

$$\text{Calories\_per\_Mile\_by\_GPS} = \frac{\text{Calores\_by\_GPS\_wk}}{\text{Miles\_by\_GPS\_wk}} \quad (3)$$

The calculated value of this calibration constant, (Calories-per-Mile_by_GPS), is stored in the patient device calibration table 440. Another example is (Calories_per_rep_per-Lb_WeightMachine_A), which also is dependent on a resistance weight machine's weight load, in Lb. For instance, the Calories_per_rep_per-Lb_WeightMachine_A can be calculated using the following formula:

$$\text{Calories\_per\_rep\_per\_lb\_WeightMachine\_A} = \frac{\text{Calories\_by\_WeightMachine\_A\_wk}}{\left(\frac{\text{Reps\_by\_WeightMachine\_A\_wk}}{\text{WeightMachine\_A\_weightload}}\right)} \quad (4)$$

The calibration ratios are considered permanent but may be re-calculated and re-saved with each therapy update. The ratio enables the HCP 40 to prescribe exercise with knowledge of the calories it will burn.

FIG. 4F shows a current conditions table 460 linked as a child to the patient preferences table 410 (FIG. 2) and populated based on information provided from a current labs table 470 (FIG. 4G), contraindications table 550 (FIG. 5E), and the allergies and conditions screen 620 (FIG. 6B). More specifically, the current conditions table 460 is populated by comparing each of the records (i.e., lab results) of the current labs table 470 against each of the records of the contraindications table 550 to identify commonality. If one of the lab results listed in the current labs table 470 satisfies one of the contraindicating conditions listed in the contraindications table 550, then the dosing controller 160 identifies the corresponding condition for input to the current conditions table 460. For example, the current labs table 470 shown in FIG. 4G shows a Glomerular Filtration Rate (GFR) measurement of 55%, which is shown in row 1 of the contraindicating conditions table 550 of FIG. 5E as a resulting contraindicating condition. Accordingly, the contraindicating condition is listed in the current conditions table 460.

The current conditions table 460 may be further populated based on responses provided by the HCP 40 in the allergies and conditions screen 620 of FIG. 6B. For example, the allergies and conditions screen 620 may include fields for entering current conditions and side effects of the patient 10.

The current conditions table 460 serves two purposes: first, to resolve conflicts between the inputs from the allergies and conditions screen 620 and the current labs table 470; and second, to provide for the recording and storing of the conditions of the patient 10 on the date of the update. Accordingly, the current conditions table 460 is provided as an interactive screen, whereby the resolution of conflicts is accomplished by a process of verification or concurrence, which is done by the HCP 40 using corresponding graphical radio buttons 462 provided in the HCP Assessment Positive column. The current conditions table 460 allows the HCP 40 to view the conditions along with the applicable lab results and make a judgment-based decision about the condition. The conditions that are fed into the current conditions table 460 from the allergies and conditions screen 620 are automatically filled with the values from the allergies and conditions screen 620.

Referring to FIG. 5A, the ADM table 510 includes a schedule of all available ADMs, which are indexed to be linked to a plurality of subtables 520, 530, 550 (FIG. 5E), 560 (FIG. 5F), as described in greater detail below. The ADM table 510 is populated with prescribing drug information 512 and scaled guidelines 514 derived from the references 196, 198 discussed above. Drug information 512 may include a Food and Drug Administration National Drug Code (FDA-NDC) number 512a, an ADM classification 512b, a generic name 512c, and a delivery method 512d. The ADM table 510 is also populated with respective scaled guidelines 514, 514a-f for each of the ADMs.

The scaled guidelines 514, 514a-f in the illustrated ADM table 510 include, but are not limited to, guidelines 562, 562a-f shown in the table entitled guideline refreshment conversion table 560 (FIG. 5F). The guidelines 562 in the illustrated example of the guideline refreshment conversion table 560 include efficacy 562a, hypoglycemia risk 562b, effect on body weight 562c, cost 562d, complexity 562e, and mealtime coverage 562f. Efficacy 562a describes how well the ADM reduces glucose concentration and hemoglobin A1c. Hypoglycemia risk 562b is the probability that the ADM will cause hypoglycemia. Weight effect 562c is the effect of the ADM on patient's weight, ranging from weight-loss at the lower end of the parameter's range to weight-gain at the upper end. Cost 562d corresponds to the dollar-cost of the ADM. Complexity 562e relates to the amount of trouble and inconvenience incurred by a patient taking the ADM. Meal coverage 562f is the degree to which an ADM is more active at meals.

Several of the guidelines 562 are provided by the references 198 in scaled form (e.g. Low, Medium, High). However, the guidelines 562 are translated to number scaled guideline values 514 between 0 and 1 in accordance with the guidance in the tabulated guideline refreshment conversion process table 560 (FIG. 5F). These numeric scaled guidelines values 514 are given names such as Scaled_Hypo_Risk, and Scaled_Weight_Effect. These scaled guideline values 514 are sent to the ADM Table 510 for storage. The ADM table 510 may occasionally be refreshed or updated to reflect revisions to the scaled guideline values 514 based on changes to the guidelines 562 in the guideline refreshment conversion table 560.

The principal of the ADM selection system 100 is to assess the applicability of each available ADM to the health status of the patient 10 based on several criteria, including patient preferences, patient medical conditions, published treatment guidelines, and availability of alternative treatment regimens, for example. An example of an ADM selection table 800 is provided in FIG. 8 for the purpose of illustrating an implementation of the ADM selection system 100. However, in practice the ADM selection system 100 may determine recommended ADMs 810 without the use of the ADM selection table 800.

Figure 7:
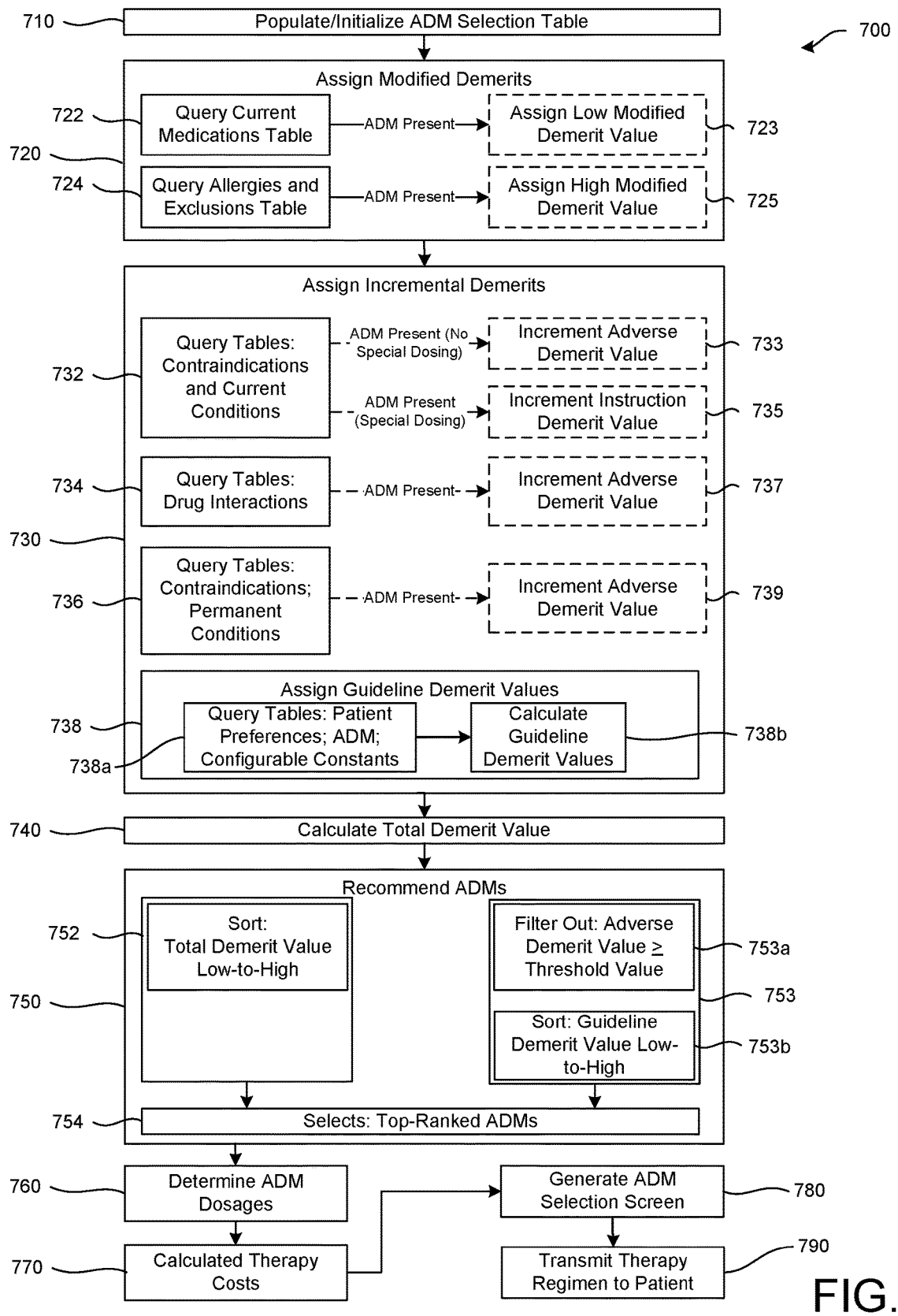
FIG. 7 is a schematic view of an ADM selection process for selecting recommended ADMs for inclusion in a treatment regimen for a patient.

Referring to FIG. 7, in some implementations, the dosing controller 160 executes an ADM selection process 700 to select available ADMs 810 for the treatment regimen of a patient 10. The ADM selection process 700 includes a first step 710 of populating an ADM selection table 800 (FIG. 8) with a listing of available ADMs 810, 810a-i, which are obtained from the ADM table 510. The ADM selection table 800 of FIG. 8 shows each ADM 810 associated with one or more demerit values 812, including an adverse demerit value 812a, an instruction demerit value 812b, a guide demerit value 812c, a modified demerit value 812d, and a total demerit value 812e. While available ADMs 810a-i are shown, the ADM selection table 800 may include more or less ADMs 810, including different types of ADMs 810 presently available or that may become available in the future for managing glucose levels. Although represented as a table 800 in the example shown, the list of available ADMs 810 may be implemented in any format. In some instances, the ADM selection table 800 is prefilled from prior iterations of the ADM selection process 700. In such cases, the first step 710 of the ADM selection process 700 includes an initialization step, whereby each of the demerit values 812 is "zeroed" and the dose notes are cleared. Each of the ADMs 810 in the ADM selection table 800 may also be associated with one or more dose notes 814, 814a-b assigned by the ADM selection process 700.

The ADM selection process 700 calculates the demerit values 812 using predetermined increment values 572 obtained from the configurable constants table 570 (FIG. 5G). As shown in FIG. 5G, the configurable constants table 570 includes an adverse demerit increment value 572a, an instruction demerit increment value 572b, and a guideline demerit value increment value 572c, along with other configurable constants, which are discussed further below. The increment values 572 for calculating each of the demerit values 812a-812c can be modified in the configurable constants table 570 by the HCP depending on a desired weight to be given to each type of demerit. In the illustrated example, the adverse demerit increment value 572a is larger than the other demerit increment values 572b, 572c. The adverse demerit increment value 572a is used for the steps of checking for adverse interactions between drugs in the ADM selection table 800 and the drug interactions table 520 (FIG. 5B), and in the step for checking for contraindicating conditions associated with each of the ADMs 810. These two steps are considered highly important and, accordingly, are configured to confer more demerits than other processes. By assigning a high value to the adverse demerits increment value 572a, ADMs 810 that are identified as having adverse interactions or contraindicating conditions are less likely to be recommended by the ADM selection system 100. In the illustrated example, the adverse demerit increment value 572a is assigned a value of 60 demerits in the configurable constants table 570. This compares with the illustrated value of 10 demerits for guideline demerits. In the current example, there are six guidelines 412a-412f (see patient preferences table 410). Accordingly, if each receives a maximum value of 10, the total guideline demerit value 812c would equal 60 demerits, which equals the total demerits of an ADM having one adverse interaction or contraindicating condition. The result of this tiered system of demerit increments 572 is that the contraindicating conditions and adverse interactions provide a coarse evaluation of the ADM under consideration and the guidelines provide a fine evaluation.

Referring back to FIG. 7, once the ADM selection table 800 is populated and initialized, a second step 720 of the ADM selection process 700 includes assigning the modified demerit values 812d for each of the ADMs 810. Here, the ADM selection process 700 queries 722 the current medications table 430 (FIG. 4C) for each ADM 810 listed in the ADM selection table 800. If an ADM 810 is included in the current medications table 430, the ADM selection process 700 assigns 723 the corresponding ADM 810 a negative (low) modified demerit value 812d, such as −200, for example. The assigning of a negative (low) modified demerit value 812d ensures that the corresponding ADM 810 will have a low total modified demerit value 812d, which will, in turn, ensure that the corresponding ADM 810 will be included among the most suitable ADMs 810 for selection from the list. In addition to adjusting the modified demerit value 812d, the ADM selection process 700 may also edit a first dose note 814a to indicate that the corresponding ADM 810 will be selected as part of the current treatment regimen for the patient 10.

The second step 720 of the ADM selection process 700 further queries 724 the allergies and exclusions table 420 (FIG. 4B) for each of the ADMs 810, 810a-810i in the ADM selection table 800. If an ADM 810, 810a-810i is listed within the allergies and exclusions table 420, then the ADM selection process 700 assigns 725 the modified demerits value 812d with a relatively high value (e.g. 200 demerits). By contrast to assigning a relatively low (e.g., negative) value (e.g., −200 demerits), a relatively high value for the demerits associated with the inclusion in the allergies and exclusions table 420 ensures that the corresponding ADM 810 will be ranked low on the list.

A third step 730 of the ADM selection process 700 includes incrementing adverse and/or instruction demerit values 812a, 812b for each of the ADMs 810. Here, the ADM selection process 700 queries 732 the contraindications table 550 (FIG. 5E) for each ADM 810 and the current conditions table 460 (FIG. 4F) to determine whether any contraindicating conditions listed in the contraindications table 550 are present in the current conditions table 460 for the patient 10. If a contraindicating condition associated with an ADM 810 is listed in the current conditions table 460, the corresponding graphical radio button 462 in the current conditions table 460 is selected, and if there are not any special dosing instructions associated with the ADM 810, then the ADM selection process 700 increments 733 the adverse demerit value 812a of the ADM by 60 demerits. On the other hand, if the corresponding ADM 810 listed in the current conditions table 460 does include special dosing instructions, then the ADM selection process 700 increments 735 the instruction demerit value 812b by 30 demerits and adds a corresponding note indicating "conditional dosing" to the dosing notes 814 (FIG. 8).

The third step 730 of the ADM selection process 700 also queries 734 the drug interactions table 520 (FIG. 5B) for each ADM 810 listed in the ADM selection table 800 to determine if any of the medications in the ADM selection table 800 interact with any of the medications that are part of the current treatment regimen. If a first ADM 810 in the selection table 800 has an adverse interaction with a second ADM 810, and the second ADM 810 is listed in the current medications table 410, the ADM selection process 700 increments 737 the adverse demerit value 812a for the first ADM by 60 demerits.

In some examples, the third step 730 of the ADM selection process 700 also queries 736 the permanent conditions table 320 (FIG. 3B) and the contraindications table 550 (FIG. 5E). The contraindicating conditions for each of the ADMs 810 in the ADM selection table 800 are compared with the permanent conditions listed in the permanent conditions table 320. If a permanent condition is included in the contraindications table 550 for the corresponding ADM and the condition appears with HCP concurrence in the current conditions table 460 (FIG. 4D), then the ADM selection process 700 increments 739 the adverse demerits value 812a for the corresponding ADM 810 by 60 demerits.

The third step 730 of the ADM selection process 700 may further assign 738 the guideline demerit value 812c for each ADM 810 in the ADM selection table 800. The assigning of the guideline demerit value 812c includes querying 738a each of the patient preferences table 410, the ADM table 510, and the configurable constants table 570 to obtain the treatment guideline rating values 412, 412a-f, the scaled guideline values 514, 514a-f, and a configurable guideline demerit increment value 572c for the corresponding ADM 810. The ADM selection process 700 may calculate 738b the guideline demerit value 812c by multiplying each of the scaled guideline values 514 by the corresponding treatment guideline rating value 412 and by the guideline demerit increment value 572c (i.e., 10) from the configurable constants table 570 for all of the guidelines listed. Accordingly, the guideline demerit value 812c for each ADM is the sum of the calculated demerit values for each of the guidelines, as provided in the following equation:

$$\text{Value}_{Guideline\ Demerit} = \Sigma(\text{Value}_{scaled}(\text{Guideline})^* \text{Value}_{Importance}(\text{Guideline})^*10) \quad (5)$$

Once ADM selection process 700 assigns the corresponding guideline demerit values 812c for each ADM 810, a fourth step 740 of the ADM selection process 700 calculates the total demerit value 812e by summing the adverse demerit value 812a, the instruction demerit value 812b, and the guideline demerit value 812c for the respective ADM. Additionally, in instances where an ADM 810 does not have a modified demerit value 812d, the total demerit value 812e will also be used as the modified demerit value 812d. Similarly, ADMs having an assigned high (e.g., positive) modified demerit value 812d (e.g., 200) may replace the corresponding total demerit value 812e.

In some implementations, a fifth step 750 of the ADM selection process 700 filters and sorts the ADMs 810 in the ADM selection table 800 based on the total demerit values 812e calculated during the fourth step 740. In some examples, the fifth step 750 of the ADM selection process 700 initially sorts 752 the ADM selection table 800 based on the total demerit values 812e and the modified demerit values 812d. Here, the initial sorting 752 orders total demerit values 812e for the ADMs 810 from lowest to highest. In some examples, any ADM 810 having a corresponding low (e.g., negative) modified demerit value 812d assigned during the second step 720 may be added to the ordered list to appear at the lowest position. For example, the ADM 810 included in the current medications table 430 (FIG. 4C) that was assigned a modified demerit value of −200, as discussed above, would appear at the top of the sorted ADM selection table 800. In some examples, an ADM having an assigned high (e.g., positive) modified demerit value 812d replaces the corresponding total demerit value 812e to ensure that the corresponding ADM 810 is ordered at the highest position. For instance, the ADM in the allergies and exclusions table that was assigned a modified demerit value of 200 would appear at the bottom of the sorted ADM selection table 800.

In lieu of the initial sorting 752 from lowest to highest based on the total demerit values 812e or the modified demerit values 812d (when applicable), the fifth step 750 of the ADM selection process 700 may optionally execute two sorting steps 753, 753a-b. The first sorting step 753a includes filtering out each ADM 810 from the ADM selection table 800 that includes a corresponding total demerit value 812e that satisfies (e.g., greater than or equal to) a demerit threshold value. As used herein, "filtering out" refers to removing an ADM 810 from the ADM selection table 800 so that the corresponding ADM 810 will not be selected as part of the treatment regimen for the patient 10. In some examples, the demerit threshold value is equal to 60 demerits and is satisfied when the total demerit value 812e is greater than or equal to 60 demerits threshold. Thus, the demerit threshold value may be selected to filter out any ADMs having contraindicating conditions listed in the contraindications table 550 that are also present in the current conditions table 460 and/or the permanent conditions table 320 for the patient 10 and/or to filter out any ADMs that interact (e.g., by accessing the drug interactions table 520) with medications the patient 10 is currently taking (e.g., by accessing the current medications table 430). The second sorting step 753b includes sorting the remaining ADMs 810 (i.e. ADMs having a total demerit value 812e less than or equal to 60 demerits) from low-to-high based on their respective guideline demerit values 812c. Accordingly, the optional sorting steps 753 sort the ADMs 810 in the ADM selection table 800 from lowest to highest based on the guideline demerit values 812c after filtering out (e.g., removing) all ADMs associated with corresponding total demerit values 812e satisfying the demerit threshold value.

With the ADM selection table 800 sorted via the initial sorting 752 based on the total demerit values 812e and/or assigned modified demerit values 812d, or the optional sorting steps 753 based on the guideline demerit values 812c after filtering out any ADMs associated with corresponding total demerit values 812e satisfying the demerit threshold value, the fifth step 750 of the ADM selection process 700 selects 754 a predetermined number of recommended ADMs 810 having the lowest total demerit values 812e or lowest guideline demerit values 812 from the sorted ADM selection table 800 for display on the display 146 associated with the HCP 40. The HCP 40 may view the predetermined number of recommended ADMs 810 to determine whether or not some or all should be included in the treatment regimen for the patient 10. The predetermined number of ADMs 810 selected may be set by the N-Finalists constant 574 (e.g., "3") in the configurable constants table 570 (FIG. 5G). Here, the number of ADMs 810 recommended by the ADM selection process 700 is in addition to any ADMs 810 that the patient 10 is currently taking (e.g., included in the current medications table 430). For instance, an ADM 810 included in the current medications table 430 may have a modified demerit value 812d equal to −200, while the next lowest-scoring ADMs 810 not included in the current medications table 430 may have total demerit values 812e equal to "10", "20", and "30", respectively. Thus, if N_Finalists is configured to a value of 3, then all four of these ADMs will be displayed in the ADM selection table 800 as recommended ADMs for inclusion in the treatment regimen of the patient 10. In this way, the HCP 40 will be able to see any ADMs the patient 10 is currently taking even if these ADMs would not have been one of predetermined number of ADMs 810 selected from the sorted ADM selection table 800 based on the initial sorting 752 or the sorting steps 753.

Once the recommended ADMs 810 are identified, the ADM selection process 700 executes a dosage step 760 to determine/calculate a dosage for each of the recommended ADMs 810 based on a comparison between a target A1c value (Target_A1c) 411b and an energy-adjusted A1c value (Energy-Adjusted_A1c) 611. The target A1c value 411b is obtained from the patient preferences table 410 (FIG. 4A) and the energy-adjusted A1c value 611 for the patient 10 is calculated using Equation 11 below.

Referring to FIG. 6C, an energy-based dosage screen 630 determines the energy-adjusted A1c value 611 by adjusting a current A1c value 632 based on fitness-related data received from the patient devices 110. The current A1c value 632 may be obtained from the current labs table 470 (FIG. 4G) and converted to a BG value (eBG) by a function subroutine that contains a published correlation as follows:

$$eBG=eBG[FUNCTION(A1c)] \qquad (6)$$

The eBG may then be converted to a value of excess carbohydrate grams per day (Carbs_XS) as follows:

$$Carbs\_XS=(eBG-TargetBG)*HTF[FUNCTION(Weight)] \qquad (7)$$

where HTF is a hypoglycemia treatment factor based on a weight of the patient 10. If the patient has a linked scale device 125, then the weight (eWeight) obtained from the smart scale 125 is substituted for clinic-measured weight throughout the program.

The excess carbohydrate grams per day (Carbs_XS) may be converted to excess energy (Calories_XS) 634 by multiplying by a Calories_Per_Carb constant 576 (e.g., 4) provided in the configurable constants table 570 (FIG. 5G). The parameter for remaining energy surplus value (Remaining_Calories_XS) 636 is initialized to the excess energy value.

The HCP 40 uses the energy-based dosing screen 630 of FIG. 6C to provide an energy-based dose adjustment for the patient 10. Here, the energy-based dose adjustment may change a dosing for each recommended ADM based on an exercise regimen for the patient 10. The exercise regimen may be obtained by tracking exercise data from the patient devices 110. The tracked exercise data may be used to determine a frequency, intensity, duration, and types of exercises associated with the patient's 10 exercise regimen. In some examples, dosing prescribed to a patient is reduced when the patient is more active. The remaining energy surplus value (Remaining_Calories_XS) 636 is adjusted by successive changes to the exercise regimen and dietary carb intake as entered by the HCP 40. This process involves a deliberate trial-and-error process, which is done interactively, preferably while the HCP 40 and the patient 10 are communicating with one another. This insures that the HCP 40 does not prescribe an exercise regimen that the patient is unwilling to comply with. Several forms of exercise may be prescribed. Also one or more of the patient devices 110 may be equipped or connected to a carbohydrate-counting database. This enables the HCP 40 to prescribe changes to the carbohydrate count in the patient's 10 diet. The decrement to the remaining energy surplus value (Remaining_Calories_XS) is tallied in the same manner as for exercise changes.

In the example shown, the HCP 40 uses the energy-based dosing screen 630 to change the exercise regimen for the patient 10 by adjusting use of Weight Machine A 635. The machine's weight load (WeightMachine_A Weight_Load) is entered in the "load or NA" entry box. The current average value of the reps per week is obtained from the patient device data table 450 (FIG. 4E) and the calibration constant (Calories_per_rep_per_Lb_WeightMachineA) is obtained from the patient device calibration table 440 (FIG. 4D). The change in exercise (Recom_Change-WeightMachine_A_reps) is input by the HCP 40. The resulting change is usually a decrement to the patient's remaining excess calories, but just in case, the sign is accounted-for. The resulting change to the remaining energy surplus value (Calories_dRx_WMA) is calculated using the calibration constant as follows:

$$\text{Calories\_dRx\_WMA} = (\text{Recom\_Change-WeightMachine\_A\_reps}) * (\text{Calories-per-rep-per-Lb\_WeightMachine\_A}) * (\text{WeightMachine\_A\_Wgt-Load}) \quad (8)$$

The decremented remaining energy surplus value (Remaining_Calories_XS) incorporating all decrements is converted back to an A1c value after each successive decrement, so that the HCP 40 can see what the predicted A1c will be. The predicted value of A1c is called the energy-adjusted A1c value (Energy_Adjusted_A1c) 611. The conversion is accomplished by the formulas below:

$$\text{Carbs\_Changed} = \frac{\text{Calories\_XS} - \text{RemainingCalorie\_XS}}{\text{Calories\_per\_Carb}} \quad (9)$$

$$\text{eBG\_Changed} = \frac{\text{Carbs\_Changed}}{\text{HTF[Function(Weight)]}} \quad (10)$$

$$\text{Energy-Adjusted\_A1C} = \text{eA1c[FUNCTION(eBG} + \text{eGB\_Changed)]} \quad (11)$$

While the example above adjusts the weight load for Weight Machine A 635 for adjusting the exercise regimen for the patient 10, other exercise regiments may not require changes in load. When the HCP 40 is satisfied with the results shown in energy-based dosage screen 630, he/she exits the screen 630 and proceeds with the patient's update process. The screen and status of the parameters remain as-is, so that the HCP 40 can return to the screen, if desired 630. The latest calculated energy-adjusted A1c value (Energy_Adjusted_A1c) 611 is used by the dosage step 760 of the ADM selection process 700 for determining/calculating the dosage for each of the recommended ADMs 810 so that the energy-based A1c adjustments are accounted for in the dose calculations. For each recommended ADM 810, the dosage step 760 further compares a sum of a current dose value (Current_Dose) and a starting dose value (Start_Dose) with a maximum allowable dose (Max_Dose). The Current_Dose may be obtained from the current medications table 430 (FIG. 4C) and the Start_Dose and the Max_Dose may be obtained from the ADM table 510 (FIG. 5A).

If an ADM is included in the current medications table 430, the energy-adjusted A1c value 611 is greater than the target A1c value, and the sum of the current dosage value and the start dosage value for the ADM is greater than the maximum dosage value, then the system recommends the current dosage value for the ADM and provides a prompt (i.e. note) to maintain the current dosage value of the ADM and to add another ADM. If the sum of the current dosage value and the start dosage value is less than or equal to the maximum dosage value and if the dosage notes are null, then the recommended dosage value is the sum of the current dosage value and the start dosage value. However, if the dosage notes are not null, such as when special dosing instructions are identified for an ADM, then the system 100 provides a prompt (i.e. note) for the HTC to consult manufacturer dosing instructions for all ADMs, except for metformin. In the case of metformin, the system 100 recommends maintaining the current dosage value and adding another ADM. In cases where the ADM is listed in the current medications table 430 and the energy-adjusted A1c value is less than or equal to the target A1c value, the system 100 recommends the current dosage for the ADM, and provides a prompt (i.e. note) recommending no change in dosage.

Once the ADM selection process 700 determines the recommended dosage values for each recommended ADM during the dosage step 760, the process executes a cost step 770 to calculate a total cost of the suggested recommended therapy based on the cost per dose and the total dosage values recommended for each recommended ADM 810. Thus, the cost step 770 may determine a cost for each recommended ADM 810 by multiplying the cost per dose times the total dosage value recommended and then sum the costs of all the recommended ADMs 810 to determine the total cost of the suggested recommended therapy. Thereafter, the ADM selection process 700 executes a selection screen step 780 for generating an ADM selection screen 640 (FIG. 6D) based on the total cost of the suggested recommended therapy calculated during the cost step 770.

Referring to FIG. 6D, the ADM selection screen 640 graphically displays a representation of the ADM selection table 800 on the display 116, 146. In the example shown, the ADM selection screen 640 includes energy-based treatment information 642 and a listing 644 of the recommended ADMs 810, 810a-c. In the example shown, the listing 644 includes a first recommended ADM 810a of Jardiance (empagliflozon), a second recommended ADM 810b of Invokana (canegliflozin), and a third recommended ADM 810c of Lantus (glargine U-100). Each recommended ADM 810 of the listing 644 on the screen 640 includes an associated recommended dosage value 646, ADM notes 647 (i.e. side-effects, dosages, adverse interactions), and a fitness level 648 indicating how well a particular ADM matches the patient 10. The HCP 40 may edit the ADM selection screen 640 to make changes to the recommended ADMs. For example, the HCP may adjust one or more of the recommend dosage values 646. The ADM selection screen 640 may also include a button 649 for opening the ADM selection table 800. Thus, the HCP 40 may select the button 649 to access the ADM selection table 800 when the HCP 40 wants to view and/or select an ADM that was not included in the recommended ADMs on the ADM selection screen 640.

Once the HCP 40 is satisfied with the recommended ADMs, the HCP 40 may save the recommended therapy regimen. Referring back to FIG. 7, the ADM selection process 700 executes a transmission step 790 to transmit the recommended therapy regimen to the patient 10. The process 700 may transmit the recommended therapy regimen to the patient 10 via at least one of a text message (SMS), electronic mail, a pre-recorded telephone message, a printed report, a web-based application, or by a downloadable application, for example. The dosing controller 160 may route the recommended therapy regimen to one or more of the patient devices 110. Using the recommended therapy regimen, the smart pill bottle 123c containing one of the recommended ADMs 810 may alert the patient 10 when the regimen specifies it is time for the patient 10 to administer the ADM 810. For instance, the bottle 123c may include a display that presents the appropriate dosage for the patient 10 to administer. The bottle 123c may also unlock when it is time for the patient 10 to administer the ADM 810. Similarly, when the recommended ADM 810 includes insulin (e.g., basal insulin such as Lantus), the dosing controller 160 may send a recommended dosage to the pen 123b that causes the pen 123b to automatically dial in a number of units associated with the recommended dosage and administer the recommended dosage to the patient 10.

Figure 9:
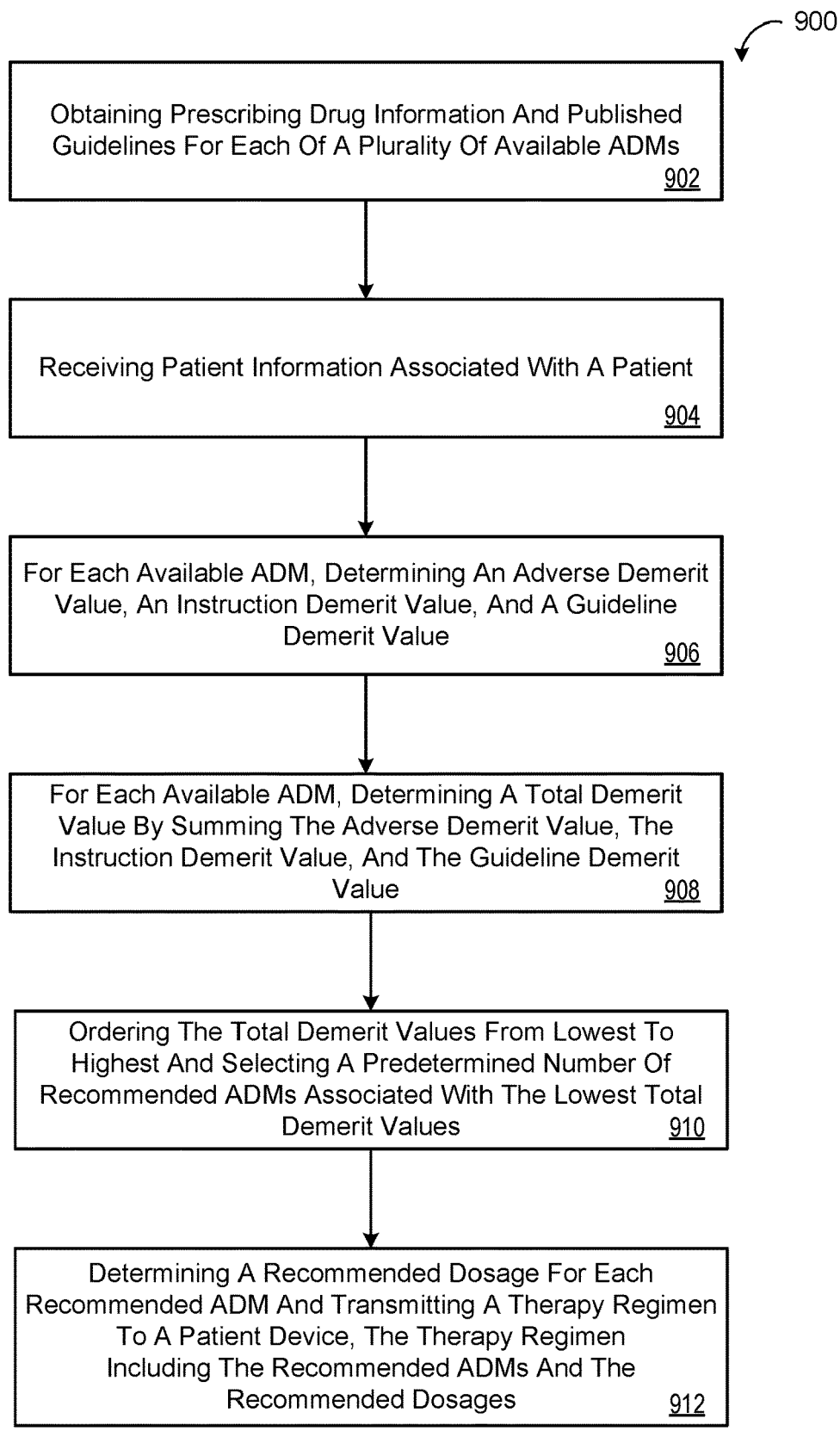
FIG. 9 is an exemplary arrangement of operations for selecting recommended ADMs and dosing for administration to a patient.

Referring to FIG. 9, a method 900 of selecting a diabetes treatment regimen includes obtaining 902, at data processing hardware 112, 132, 142, prescribing drug information and published guidelines for each of a plurality of Anti-Diabetes Medications (ADMs) 810 available for managing glucose levels. The ADMs may be used to manage glucose levels in outpatients having Type 2 Diabetes or for those who are at risk of developing Diabetes. The method 900 includes the data processing hardware 112, 132, 142 receiving 904 patient information associated with a patient 10 seeking selection and dosing of one or more of the available ADMs 810.

For each available ADM, the method 900 includes the data processing hardware 112, 132, 142 determining 906 an adverse demerit value 812a, an instruction demerit value 812b, and a guideline demerit value 812c based on the patient information and the prescribing drug information 196 and published guidelines 198 for the corresponding ADM 810, and determining 908 a total demerit value 812e by summing the adverse demerit value 812a, the instruction demerit value 812b, and the guideline demerit value 812c. The method 900 also includes the data processing hardware 112, 132, 142 ordering 910 the total demerit values 812e for the available ADMs 810 from lowest to highest and selecting a predetermined number of recommended ADMs associated with the lowest total demerit values 812e.

The method 900 also includes the data processing hardware 112, 132, 142 determining 912 a recommended dosage for each recommended ADM 810 and transmitting a therapy regimen to a patient device associated with the patient, the therapy regimen including the recommended ADMs 810 and the recommended dosage for each recommended ADM 810.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A computer-implemented method executed on data processing hardware that causes the data processing hardware to perform operations comprising:
   receiving patient information associated with a patient seeking selection and dosing of one or more of a plurality of available Anti-Diabetes Medications (ADMs) for managing glucose levels;
   obtaining treatment guideline ratings each assigned by the patient that measures a subjective level of importance to the patient for a corresponding treatment guideline;
   obtaining prescribing drug information and published guidelines for each of the plurality of available ADMs;
   for each corresponding available ADM of the plurality of available ADMs:
      obtaining scaled guideline values for the corresponding available ADM based on the prescribing drug information and the published guidelines, each scaled guideline value associated with a corresponding treatment guideline rating;
      determining a guideline demerit numerical value for the corresponding available ADM by multiplying, for each treatment guideline rating, the treatment guideline rating times the corresponding scaled guideline value and a guideline demerit increment value; and
      determining a total demerit value for the corresponding available ADM based on the guideline demerit numerical value determined for the corresponding available ADM;
   ordering the total demerit numerical values in numerical order for the available ADMs from the lowest total demerit numerical value to the highest total demerit numerical value;
   selecting a predetermined number of recommended ADMs associated with the lowest total numerical demerit values from the plurality of available ADMs;
   determining a recommended dosage for each recommended ADM based on the patient information, the prescribing drug information, and the published guidelines; and transmitting, via a network, instructions to an administration device associated with one of the recommended ADMs, the instructions when received by the administration device causing the administration device to configure a doser of the administration device to administer the recommended dosage of the one of the recommended ADMs to the patient.

2. The computer-implemented method of claim 1, wherein the patient information comprises:
a current medications list including a list of medications and corresponding dosages the patient is currently prescribed; and
medical conditions associated with the patient.

3. The computer-implemented method of claim 2, wherein the patient information further comprises at least one of:
a target glucose range for the patient;
a target A1c value for the patient;
a preferred minimum monthly treatment cost; or
a preferred maximum monthly treatment cost.

4. The computer-implemented method of claim 2, wherein the patient information further comprises:
one or more glucose values for the patient measured by a glucometer or continuous glucose monitor in communication with the data processing hardware; or
an A1c value for the patient.

5. The computer-implemented method of claim 1, wherein the treatment guideline ratings comprise at least one of:
a cost rating;
a body weight rating;
a treatment regimen complexity rating;
a treatment efficacy rating;
a mealtime coverage needs rating; or
a hypoglycemia rating.

6. The computer-implemented method of claim 1, wherein the prescribing drug information and published guidelines comprises, for each corresponding available ADM of the plurality of available ADMs:
one or more contraindicating conditions associated with the corresponding available ADM; and
a list of medications that interact with the corresponding available ADM.

7. The computer-implemented method of claim 6, wherein the operations further comprise, for each corresponding available ADM of the plurality of available ADMs:
assigning an adverse demerit increment value when the medical conditions associated with the patient indicate that the patient currently has any of the contraindicating conditions associated with the corresponding available ADM; and
assigning the adverse demerit increment value when the current medications list indicate that the patient is currently taking at least one of the medications that interact with corresponding available ADM,
wherein determining the total demerit numerical value for the corresponding available ADM is further based on a sum of each adverse demerit increment value assigned to the corresponding available ADM.

8. The computer-implemented method of claim 1, wherein the operations further comprise:
receiving exercise data from a fitness tracker associated with the patient; and
adjusting the recommended dosage for at least one of the recommended ADMs based on the received exercise data.

9. The computer-implemented method of claim 1, wherein the operations further comprise:
obtaining a list of excluded ADMs that the patient is either allergic to or is excluded from the treatment regimen for the patient; and
for at least one corresponding available ADM of the plurality of available ADMs:
determining the corresponding available ADM is on the list of excluded ADMs; and
assigning a high modified demerit numerical value to the corresponding available ADM; and
replacing the total demerit numerical value for the corresponding available ADM with the assigned high modified demerit value.

10. The computer-implemented method of claim 1, wherein the operations further comprise transmitting a therapy regimen from the data processing hardware to a patient device associated with the patient and in communication with the data processing hardware via the network, the therapy regimen comprising the recommended ADMs and the recommended dosage for each recommended ADM, the therapy regimen when received by the patient device causing the patient device to display the recommended ADMs and the recommended dosage for each recommended ADM on a patient interface executing on the patient device.

11. A system comprising:
data processing hardware; and
memory hardware in communication with the data processing hardware and storing instructions that when executed on the data processing hardware causes the data processing hardware to perform operations comprising:
receiving patient information associated with a patient seeking selection and dosing of one or more of a plurality of available Anti-Diabetes Medications (ADMs) for managing glucose levels;
obtaining treatment guideline ratings each assigned by the patient that measures a subjective level of importance to the patient for a corresponding treatment guideline;
obtaining prescribing drug information and published guidelines for each of the plurality of available ADMs;
for each corresponding available ADM of the plurality of available ADMs:
obtaining scaled guideline values for the corresponding available ADM based on the prescribing drug information and the published guidelines, each scaled guideline value associated with a corresponding treatment guideline rating;
determining a guideline demerit numerical value for the corresponding available ADM by multiplying, for each treatment guideline rating, the treatment guideline rating times the corresponding scaled guideline value and a guideline demerit increment value; and
determining a total demerit value for the corresponding available ADM based on the guideline demerit numerical value determined for the corresponding available ADM;
ordering the total demerit numerical values in numerical order for the available ADMs from the lowest total demerit numerical value to the highest total demerit numerical value;
selecting a predetermined number of recommended ADMs associated with the lowest total numerical demerit values from the plurality of available ADMs;

determining a recommended dosage for each recommended ADM based on the patient information, the prescribing drug information, and the published guidelines; and transmitting, via a network, instructions to an administration device associated with one of the recommended ADMs, the instructions when received by the administration device causing the administration device to configure a doser of the administration device to administer the recommended dosage of the one of the recommended ADMs to the patient.

12. The system of claim 11, wherein the patient information comprises:
a current medications list including a list of medications and corresponding dosages the patient is currently prescribed; and
medical conditions associated with the patient.

13. The system of claim 12, wherein the patient information further comprises at least one of:
a target glucose range for the patient;
a target A1c value for the patient;
a preferred minimum monthly treatment cost; or
a preferred maximum monthly treatment cost.

14. The system of claim 12, wherein the patient information further comprises:
one or more glucose values for the patient measured by a glucometer or continuous glucose monitor in communication with the data processing hardware; or
an A1c value for the patient.

15. The system of claim 11, wherein the treatment guideline ratings comprise at least one of:
a cost rating;
a body weight rating;
a treatment regimen complexity rating;
a treatment efficacy rating;
a mealtime coverage needs rating; or
a hypoglycemia rating.

16. The system of claim 11, wherein the prescribing drug information and published guidelines comprises, for each corresponding available ADM of the plurality of available ADMs:
one or more contraindicating conditions associated with the corresponding available ADM; and
a list of medications that interact with the corresponding available ADM.

17. The system of claim 16, wherein the operations further comprise, for each corresponding available ADM of the plurality of available ADMs:

assigning an adverse demerit increment value when the medical conditions associated with the patient indicate that the patient currently has any of the contraindicating conditions associated with the corresponding available ADM; and assigning the adverse demerit increment value when the current medications list indicate that the patient is currently taking at least one of the medications that interact with corresponding available ADM, wherein determining the total demerit numerical value for the corresponding available ADM is further based on a sum of each adverse demerit increment value assigned to the corresponding available ADM.

18. The system of claim 11, wherein the operations further comprise:
receiving exercise data from a fitness tracker associated with the patient; and
adjusting the recommended dosage for at least one of the recommended ADMs based on the received exercise data.

19. The system of claim 11, wherein the operations further comprise:
obtaining a list of excluded ADMs that the patient is either allergic to or is excluded from the treatment regimen for the patient; and
for at least one corresponding available ADM of the plurality of available ADMs:
determining the corresponding available ADM is on the list of excluded ADMs; and
assigning a high modified demerit numerical value to the corresponding available ADM; and
replacing the total demerit numerical value for the corresponding available ADM with the assigned high modified demerit value.

20. The system of claim 11, wherein the operations further comprise transmitting a therapy regimen from the data processing hardware to a patient device associated with the patient and in communication with the data processing hardware via the network, the therapy regimen comprising the recommended ADMs and the recommended dosage for each recommended ADM, the therapy regimen when received by the patient device causing the patient device to display the recommended ADMs and the recommended dosage for each recommended ADM on a patient interface executing on the patient device.

* * * * *